United States Patent
Thiebaud et al.

(10) Patent No.: US 11,092,148 B2
(45) Date of Patent: Aug. 17, 2021

(54) DEVICE FOR EXTRACORPOREAL BLOOD TREATMENT

(71) Applicant: DEBIOTECH S.A., Lausanne (CH)

(72) Inventors: Pierre Thiebaud, Cressier (CH); Olivier Magnenat, Lausanne (CH); Reto Cueni, Cugy (CH); Frédéric Neftel, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 235 days.

(21) Appl. No.: 16/196,339

(22) Filed: Nov. 20, 2018

(65) Prior Publication Data

US 2019/0120261 A1   Apr. 25, 2019

Related U.S. Application Data

(62) Division of application No. 14/439,382, filed as application No. PCT/IB2013/059744 on Oct. 29, 2013, now Pat. No. 10,138,911.

(30) Foreign Application Priority Data

Oct. 29, 2012   (WO) .................. PCT/IB2012/055972

(51) Int. Cl.
| | |
|---|---|
| F04B 43/00 | (2006.01) |
| F04B 43/12 | (2006.01) |
| A61M 1/26 | (2006.01) |
| F04B 53/22 | (2006.01) |
| A61M 1/16 | (2006.01) |
| A61M 1/34 | (2006.01) |

(Continued)

(52) U.S. Cl.
CPC ......... F04B 43/0009 (2013.01); A61M 1/267 (2014.02); F04B 43/12 (2013.01); F04B 53/22 (2013.01); A61M 1/16 (2013.01); A61M 1/34 (2013.01); A61M 1/3434 (2014.02); A61M 1/36 (2013.01); A61M 2205/12 (2013.01); A61M 2205/3317 (2013.01); A61M 2205/3324 (2013.01); A61M 2205/3331 (2013.01); A61M 2205/3334 (2013.01); A61M 2205/50 (2013.01); F15B 15/02 (2013.01)

(58) Field of Classification Search
CPC .......... F15B 15/02; F04B 43/12; F04B 53/22; A61M 1/267; F16D 3/205
USPC ....................... 417/477.2, 359; 464/110, 112
See application file for complete search history.

(56) References Cited

U.S. PATENT DOCUMENTS

| | | | | |
|---|---|---|---|---|
| 4,861,242 A | * | 8/1989 | Finsterwald | ........ F04B 43/1253 417/477.2 |
| 6,186,665 B1 | | 2/2001 | Maher et al. | |

(Continued)

FOREIGN PATENT DOCUMENTS

| | | |
|---|---|---|
| EP | 0 471 000 B1 | 12/1998 |
| EP | 1 648 536 B1 | 5/2011 |
| EP | 1 195 171 B1 | 8/2012 |

OTHER PUBLICATIONS

International Preliminary Report on Patentability and Written Opinion of the International Searching Authority dated May 5, 2015, issued in International Application No. PCT/IB2013/059744.

(Continued)

*Primary Examiner* — Charles G Freay
(74) *Attorney, Agent, or Firm* — Nixon & Vanderhye P.C.

(57) ABSTRACT

The invention relates to a system for treating blood, which includes a single cassette capable of carrying out the various CRRT treatments.

16 Claims, 14 Drawing Sheets

Figure 1:
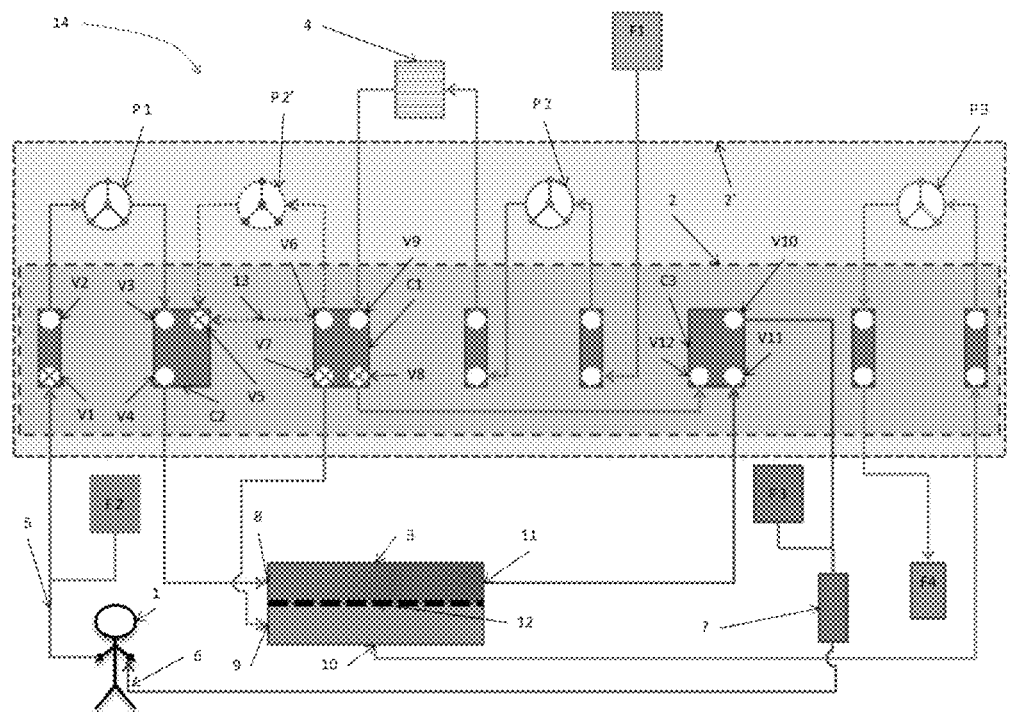

(51) Int. Cl.
*A61M 1/36* (2006.01)
*F15B 15/02* (2006.01)

(56) References Cited

U.S. PATENT DOCUMENTS 6,375,577 B1 * 4/2002 Smith .................... F16D 1/108
464/106
7,018,182 B2 * 3/2006 O'Mahony ......... F04B 43/1253
417/476

OTHER PUBLICATIONS

Substantive Examination Report dated Nov. 28, 2018, issued in Philippine Patent Application No. 1/2015/500954.

* cited by examiner

DEVICE FOR EXTRACORPOREAL BLOOD TREATMENT

The present application is a divisional application that claims priority to application Ser. No. 14/439,382 filed on Apr. 29, 2015, which is the United States national stage application of International patent application PCT/IB2013/059744 filed on Oct. 29, 2013 designating the United States, and claims foreign priority to International patent application PCT/IB2012/055972 filed on Oct. 29, 2012, the contents of each of which are hereby incorporated by reference.

FIELD OF THE INVENTION

The invention relates to a device for extracorporeal blood treatment. The device comprises in particular a cassette permitting the distribution of the fluids in order to carry out said treatment, and means for improving the efficacy of said device that can be used separately and/or with said cassette.

PRIOR ART

There are several possible reasons why a person may suffer from renal insufficiency, in which the temporary/permanent and partial/total shutdown forces this person to use extracorporeal devices that completely or partially replace the patient's own kidneys. Dialysis is a technique of blood purification. It allows a patient suffering from such a disease to eliminate impurities such as urea and excess water from the organism, which would usually have been eliminated by normally functioning kidneys.

It is possible to differentiate between two types of renal insufficiency linked to the duration of the disease and sometimes requiring considerably different treatments, i.e. chronic renal insufficiency and acute renal insufficiency. Chronic renal insufficiency means that the patient has to undergo treatment at regular intervals for life. For this purpose, the patient can carry out this treatment at a medical center or at home using an apparatus for peritoneal dialysis or hemodialysis. Acute renal insufficiency is a temporary disease in which the patient requires an apparatus to temporarily replace the functions of his kidneys. In this case, the patient undergoes continuous renal replacement therapy. Peritoneal dialysis and continuous renal replacement therapy are very different, as are the techniques and/or devices used:

Peritoneal dialysis uses the patient's peritoneum, which is the natural membrane enclosing the walls of the abdomen and the organs situated in the abdomen (liver, intestines, etc.). The peritoneal membrane has a very large surface area and comprises a very large number of blood vessels. It thus performs the role of natural filter. Numerous patents disclose systems for carrying out peritoneal dialysis, some of which use cassettes (EP 1 648 536 A2, EP 0 471 000 B1, EP 1 195 171 B1, EP 1 648 536 B1) for injecting fluid into the patient's peritoneum and removing the fluid therefrom.
  Continuous renal replacement therapy (CRRT) is a method in which blood has to be removed continuously from the patient and treated by means of a filter, generally a dialyzer, after which the treated blood is re-injected into the patient. Two main principles are used by virtue of the filter:
    Diffusion allows solute molecules to pass through a semipermeable membrane according to a concentration gradient. The solutes pass from the more concentrated medium (the blood) to the less concentrated medium (the dialysate) and are distributed uniformly on each side of the membrane of the filter.
    Convection permits the simultaneous transfer of water and of its solute content through the semipermeable membrane by virtue of the hydrostatic pressure gradient across the membrane. Thus, the solutes pass from the medium where the pressure is highest (blood compartment) to the medium where the pressure is lowest (dialysate compartment).

Various techniques of continuous renal replacement therapy exist that use one or both of these principles: slow continuous ultrafiltration (SCUF), continuous venovenous hemofiltration (CVVH), continuous venovenous hemodialysis (CVVHD), continuous venovenous hemodiafiltration (CVVHDF), therapeutic plasma exchange (TPE) and hemoperfusion (also called blood detoxification). At present, no device is able to provide all of these treatments without the intervention of trained medical staff. In addition, these techniques are mainly used in intensive care environments. Unfortunately, these techniques make use of cumbersome appliances that can interfere with the proper conduct of other treatments carried out on the patient. Moreover, these appliances are complex and comprise numerous consumables, and they require substantial changes to be made in order to carry out the various techniques mentioned above. This involves the personnel receiving special training.

General Description of the Invention

The invention relates to numerous improvements for medical devices, means and/or methods used for medical devices.

The present application claims the priority of the application bearing the number PCT/IB2012/055972 filed on Oct. 29, 2012 in the name of Debiotech, the entire content of which application must be regarded as forming part of the present application.

A first aspect of the invention relates to a single cassette by means of which it is possible to carry out one or all of the various techniques of continuous renal replacement therapy: slow continuous ultrafiltration (SCUF), continuous venovenous hemofiltration (CVVH), continuous venovenous hemodialysis (CVVHD), continuous venovenous hemodiafiltration (CVVHDF), therapeutic plasma exchange (TPE) and hemoperfusion. In one embodiment, the device can also be used in the context of peritoneal dialysis, where some elements and/or features might not be used or could be used for other functions, such as taking samples or the like. In an embodiment, the cassette is partially or completely integrated in the dialysis apparatus, or some of these elements form part of said apparatus (for example the pumping system, the sensors, the filter, etc.) or are physically separate from the cassette (for example the filter, supply means, reservoirs, sensors, heating means, etc.) or are optional. Preferably, said cassette and the dialysis apparatus are both separate. The cassette can be discarded whereas the apparatus can be reused. This means that the cassette can be replaced at each treatment (single use, replacement of the cassette after each use) and that the apparatus can be used several times with different cassettes. Said cassettes are designed to cooperate physically and/or mechanically with the apparatus and/or vice versa. In addition, the use of a single cassette makes it possible to simplify the use of said device, to reduce operator errors by virtue of this simplification, to automate the treatment without the intervention of medical staff, to limit the number of cassette types, to simplify programming, to permit the use of the device at the patient's home and/or to limit the space taken up by the device.

According to a second aspect of the invention, the device can comprise only 3 main pumps in order to carry out at least one or all of the techniques cited in the prior art (SCUF, CVV, CVVH, CVVHDF, TPE and hemoperfusion).

According to one embodiment, the device comprises a blood filtration means, at least one liquid supply means, two patient tubes, namely an outlet tube for collecting the blood to be treated, and an inlet tube for re-injecting the treated blood into the patient, (or a single tube in the case of peritoneal dialysis or a tube with two separate lumens), a filtrate recovery means, three fluid pumps, a cassette composed of channels and valves for directing the fluids, and a controller which controls the pumps and the opening and the closure of said valves depending on the desired treatment.

Said cassette comprises at least one distribution chamber comprising a single inlet channel, at least two outlet channels and at least two connection chambers comprising at least two inlet channels and an outlet channel. Preferably, said distribution chamber comprises an inlet channel and three outlet channels controlled by the controller (in an automatic, programmed and/or controlled manner) so as to allow a fluid to be injected into the blood filtration means, into the blood before the blood filtration means (pre-dilution) and/or after the blood filtration means (post-dilution). By virtue of this distribution chamber, the device can carry out any treatment by dialysis without the medical staff (or other specialists) being present in order to configure the specific connections for each treatment.

Said system additionally comprises at least three flow paths. The first flow path connects said blood filtration means to the filtrate recovery means. It comprises a series of channels and a dedicated pump. The second flow path is dedicated to the circulation of the blood. It comprises at least two connection chambers, a series of channels, said blood filtration means, said patient tubes and a dedicated pump. The third flow path comprises a liquid supply means, at least one dedicated pump, a series of channels, a distribution chamber and, optionally, a heating means.

Said distribution chamber comprises at least three separate outlet channels:
  a first outlet channel supplying the second flow path upstream of the filtration means (for carrying out a pre-dilution of the blood before it is filtered by the filtration means),
  a second outlet channel supplying the second flow path downstream of the filtration means (for carrying out a post-dilution of the blood after it has been filtered by the filtration means), and
  a third outlet channel supplying said filtration means.

In one embodiment, the two connection chambers and the distribution chamber are supplied with positive pressure by two pumps that are placed upstream of said chambers.

Said first connection chamber makes it possible to connect the second flow path to the third flow path upstream of the filter (pre-dilution technique). It comprises an inlet channel coming from the second flow path, an inlet channel coming from the third flow path, and an outlet channel allowing the blood to flow in the direction of the filter, and said inlet channel coming from the third flow path can comprise a valve controlled by said controller, a flow restrictor and/or a pump.

Said second connection chamber makes it possible to connect the second flow path to the third flow path downstream of the filter (post-dilution technique). It comprises an inlet channel coming from the second flow path after its passage through the filter, an inlet channel coming from the third flow path, and an outlet channel in the direction of the patient.

According to certain embodiments, the invention can additionally comprise:
  A supply means for injecting an anticoagulant into the second flow path, either directly into the patient outlet tube, or farthest upstream in the cassette by virtue of a connection chamber that allows the anticoagulant to be mixed with the blood (fluid of the second flow path), and/or
  A supply means by which a product inhibiting the anticoagulant is injected into the second flow path, either directly into the patient inlet tube, or farthest downstream in the cassette by virtue of a connection chamber that allows said product to be mixed with the blood (fluid of the second flow path).

A third aspect of the invention relates to the structure of the cassette, when a flow path (coming, for example, from a liquid supply means) is connected to another flow path, the cassette preferably comprises a connection chamber permitting the intersection of said two flow paths. This connection chamber can thus permit mixing of the fluids coming from said flow paths. In addition, at least one of said inlet channels of said connection chamber can comprise a valve, such that the controller can select the one or more defined fluids that will flow into the connection chamber depending on the treatment that is desired, programmed or controlled.

According to a fourth aspect of the invention, a heating means is situated in the third flow path between the main pump of the dialysate and the distribution chamber. Said heating means is preferably a flexible bag supplied with positive pressure by said pump. In one embodiment, a second pump is located between the distribution chamber and a connection chamber. Preferably, the distribution chamber is connected to a first and second connection chamber. The first connection chamber makes it possible to carry out a pre-dilution of the fluid flowing in the second flow path (that is to say dilution of the blood before the filtering means), while the second connection chamber permits a post-dilution of the fluid of said second flow path (that is to say dilution of the blood after the filtering means). The first pump is a precision pump by which it is possible to know precisely the quantity of fluid that will be mixed in the blood at pre-dilution and post-dilution. The second pump is located downstream of one of the two connection chambers, while the other connection chamber or both connection chambers can comprise a valve. This second pump is a distributor pump by which it is possible to distribute a defined quantity of fluid between the first and second connection chambers. This type of system can comprise one or more other connection chambers. Preferably, the system comprises a pressure sensor, and the heating means can serve as temporary storage means.

To optimize the function of the treatment system, the invention likewise discloses the following elements, which can be used with or without the cassette described above:
  a means and a method for calibration of the pumps of the first and third flow paths,
  a pressure sensor offset from the flow path,
  an energy-saving linear actuator,
  a drive device used for the peristaltic pumps,
  a means of damping the pressure peaks.

Means and Method for Calibration of the Pumps and/or Sensors of the First and Third Flow Paths:

In certain techniques of continuous renal replacement therapy, it is essential to know precisely the volume quantity injected into and withdrawn from the third and first flow paths. The devices usually comprise two balances, namely a balance dedicated to the dialysate and another one dedicated to the filtrate. The present invention can comprise the same system of balances, but these balances are very sensitive and bulky (since they have to be able to contain all of the fluids). Other devices have cavities of which the volume capacity is known with precision. These cavities are located directly on the first and third flow paths (an intermediate wall being used so as not to mix the two fluids) and they are successively filled with and then emptied of the fluids of said flow paths. When the cavity fills with dialysate, the cavity empties itself of the filtrate previously contained in said cavity and/or vice versa. These devices can comprise several of these cavities. However, in contrast to the device of the present invention, these devices do not permit a continuous function, and instead they function in a succession of steps of filling and emptying of the fluids contained in said cavities.

According to a fifth aspect of the invention, the treatment system has a means for calibrating said pumps in order to ensure that said volumes are known with precision. The system comprises:

at least two volume-measuring means (sensor, mass flow system, volume pump, peristaltic pump, balance, etc.), of which one measures the quantity of liquid flowing through the third flow path, and one measures the quantity of liquid flowing through the first flow path;

a means of taking samples from the first and third flow paths;

a common means of measuring the sampled volumes.

Said common measurement means measures the quantity of fluid sampled by the sampling means and makes it possible to compare the sampled volumes and to calibrate said pumps and/or said volume-measuring means.

In one embodiment, said pumps are regarded as said volume-measuring means since each actuation corresponds to a given volume.

In another embodiment, the volume sensors are separate from the pumps and continuously measure the volumes delivered by said pumps. In the event of drifting of the pumped volumes, the controller is able to correct the actuation of said pumps in order to correct the volumes or the volume differential.

A sixth aspect of the invention relates to a method for the calibration of pumps used to deliver the fluids of the first and third flow paths and/or of the sensors placed in said flow paths. The method additionally allows said pumps to be calibrated before and/or during the treatment.

Pressure Sensor Offset from the Flow Path:

A seventh aspect of the invention relates to a means for measuring the pressure of a fluid. In one embodiment, the treatment system comprises at least one pressure sensor in at least one of said flow paths. The present document discloses a fluid distribution system (preferably a cassette) which makes it possible to sample and/or deliver a fluid F11 and to measure the pressure of said fluid F11. The system comprises a rigid body composed of at least one flow path through which said fluid F11 flows, at least one channel separate from said flow path. Said channel makes it possible to connect said flow path to a measuring zone. The system can comprise at least one opening covered by a flexible membrane forming said measuring zone. The membrane is designed to receive a pressure sensor.

A fluid F12 different than the fluid F11 is contained in said measuring zone. The fluid F12 at least partially fills the measuring zone and/or said channel. Said fluid F12 makes it possible to transmit the pressure of the fluid F11 to said membrane.

The aim of this channel is that the fluid F11 cannot come into contact with said membrane or that the fluid F11 at least partially wets said membrane. Thus, the channel can be designed in such a way that said fluid F11 limits, slows and/or controls the flow of the fluid F11 through said channel. It has a shape and a length permitting this function and/or can comprise a means for containing the fluid F11 (such as a membrane, a hydrophilic filter, a hydrophobic filter, etc.). Preferably, the measuring zone is filled with both fluids F11 and F12 and/or the fluids F11 and F12 are in contact with the membrane.

Energy-Saving Linear Actuator:

In one embodiment, the treatment system comprises at least one energy-saving linear actuator. The present document discloses an innovative principle for controlling a linear actuator that consumes a small amount of energy and for controlling the position of a valve. This actuator can be included in a system as described above, but also in any device using a linear actuator. In particular, the actuator must offer two basic positions, namely valve closed (where the piston is in a first position) and valve opened (where the piston is in a second position). The piston can also have a third position corresponding to a state in which the piston of the actuator is disengaged from the foot of the valve.

To ensure the function of linear actuator, two different techniques are normally used: the electromagnet or the brushless motor mounted with an endless screw and a nut. The main disadvantage of these two techniques is that they consume energy in order to maintain a position. The present invention discloses a linear actuator comprising at least two stationary positions with low energy consumption and a rapid return to a safety position. In addition, the actuator disclosed by the present document does not consume any energy, or only a small amount of energy, to maintain its different positions.

The eighth aspect of the invention thus relates to a linear actuator comprising a rotary electric motor, a piston, and means which are interposed between the electric motor and the piston and transform the rotation movement of the motor into a linear displacement of the piston. Said interposed means comprise at least one peripheral ramp arranged inside said piston, at least one guide means allowing the piston to guide the translation movement, and at least one bearing means fixed directly or indirectly to the rotor of said electric motor. Said bearing means is designed in such a way as to cooperate with said peripheral ramp. In one embodiment, said actuator additionally comprises at least one compression means that exerts a force against the piston in the direction of the distal end of the piston. The ramp comprises at least one threshold for obtaining at least one stationary position without consuming energy. At least one threshold is positioned at the summit of said ramp. In a preferred embodiment, this threshold is followed by a passage allowing the piston to free itself of the stresses exerted by the bearing means.

According to a ninth aspect of the invention, the actuator is able to guarantee a given occlusion pressure when the valve is in the closed position. The position of the valve with no contribution from the actuator is preferably a closed position. To guarantee good occlusion, the actuator has a compression means for ensuring a sufficient occlusion pressure of the valve against its seat when the piston is in the first position. Said compression means permits a third position (when the piston is not engaged with the valve) in which the piston is located farther away from the support of the actuator. The passage from the third position to the first position is effected when the piston engages with the valve. In other words, when the cassette is placed in the device. Thus, the compression means compels the piston to exert an initial force against the valve, which transmits this force against the seat of the valve, guaranteeing an occlusion of the flow path when the piston is in the first position.

In one embodiment, said compression means can be on the support of the actuator or in said piston. In other words, when said piston of the actuator is engaged with the foot of the valve, i.e. in the first position, a compression means ensures prestressing in order to guarantee good occlusion. Said compression means can be mounted in the actuator or on the support of the actuator, said compression means making it possible to obtain a third position in which the piston of the actuator is farther from the support of the actuator than in the first and second positions. The occlusion pressure depends on the design of the valve and on the dimensions of the compression means.

Drive Device used for the Peristaltic Pumps:

A tenth aspect of the invention relates to a drive device used for a pump.

During the use of said treatment system, the cassette is inserted in a cycler which comprises sensors, linear actuators (for opening and closing the valves), and means for driving the rollers of the peristaltic pump. In order to guarantee correct functioning of the system, it is important that all the elements are correctly aligned (sensor, actuator, actuation means, etc.). Now, there may be a difference between the theoretical central point of the head of the pump and the actual central point. This difference creates problems in the alignment of the actuators and of the sensors, respectively, on the valves and the measuring zones of the cassette. Thus, guide means make it possible to overcome this problem of alignment for the sensors and actuators but transpose the difference to the pumping system. Thus, stresses of a greater or lesser degree may be exerted on the elements of the pump, which may affect the precision of the peristaltic pump. The phenomenon is all the more pronounced when the pumps are present in large number.

In order to relax the manufacturing tolerances and to guarantee the precision of the peristaltic pumps, the invention discloses a drive device for the pumps which comprises a floating shaft driven by a drive means fixed to a rotor. The floating shaft comprises a rigid assembly of base and cover that forms a cavity inside which said drive means is at least partially circumscribed. In addition, said drive means comprises a rigid body designed in such a way as to cooperate with the walls of said cavity in order to permit a restricted freedom of the floating shaft with respect to the shaft of said rotor. The floating shaft allows the axis of the pumping system to be off-centered, so as to minimize or even eliminate all stresses exerted by the shaft of the pump on the theoretical pumping shaft of the cassette.

Means for Damping the Pressure Peaks:

An eleventh aspect of the invention relates to a means for damping the pressure peaks.

The quantity of a pumped fluid can be influenced by the constituent elements of the system. These elements can be the pumping mechanism, the valve mechanism, the liquid supply means (tubes, reservoirs, etc.). In particular, the pumping mechanism of a peristaltic pump can cause variations in pressure. Thus, a pressure wave forms and spreads through the one or more flow paths each time the rollers come into contact with the flexible tube. This spread is attenuated or reinforced by a number of factors such as the type of liquid, the length of the flow path, the restrictions, the type of materials of the system, the quantity of liquid delivered by the pumping mechanism, the type of pump, the characteristics of its components (flexible tube, etc.), the pressure downstream of the pump, etc.

One of the improvements of the invention is to reduce the amplitude of the pressure peaks and the influence thereof on the quantity pumped. This reduction is achieved by adding to the flow path a means designed to absorb the pressure peaks.

Another advantage of this reduction of the peaks is likewise that of obtaining a more constant pressure, which increases patient comfort. In this embodiment, the peaks can be damped downstream of the pump during an injection toward the patient, and upstream when the pump withdraws a fluid coming from the patient (in particular during peritoneal dialysis).

This damping means can be a cavity filled with a compressible fluid such as air. This damping means can be a flexible element that is deformed by the pressure peaks and returns to a state of equilibrium. This flexible element can, for example, be a polymer membrane in the wall of the flow path.

In the present document, the various aspects of the invention can be the subject matter of independent or dependent claims which may or may not relate to any system of medical treatment.

LIST OF FIGURES

The invention will be better understood below on the basis of a number of illustrative examples. It goes without saying that the invention is not limited to these embodiments.

Figure 2:
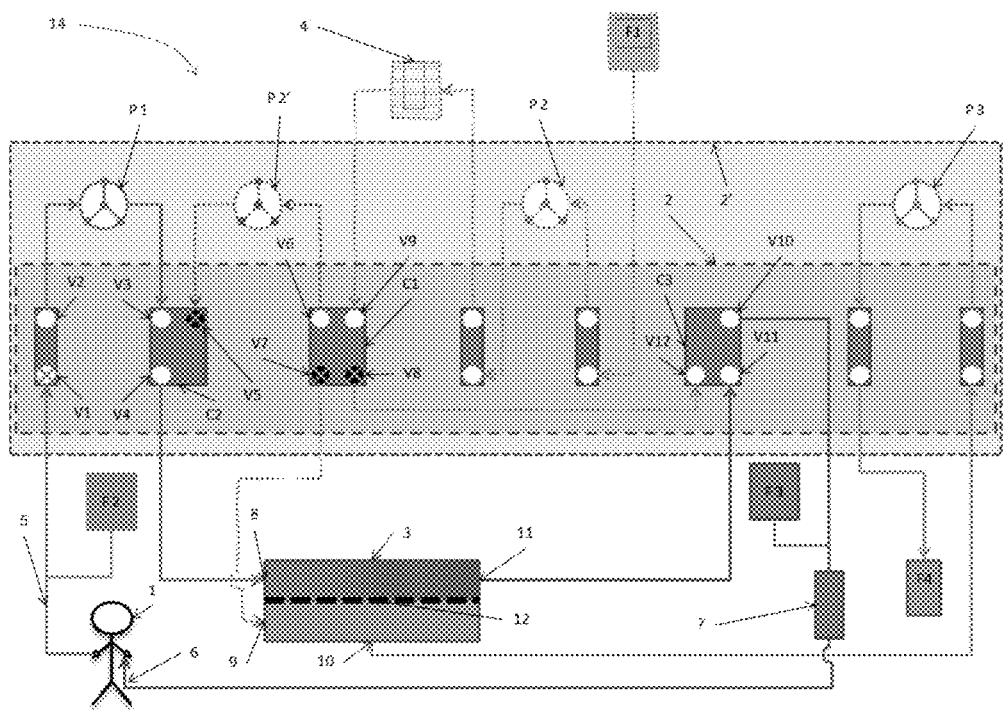
Figure 3:
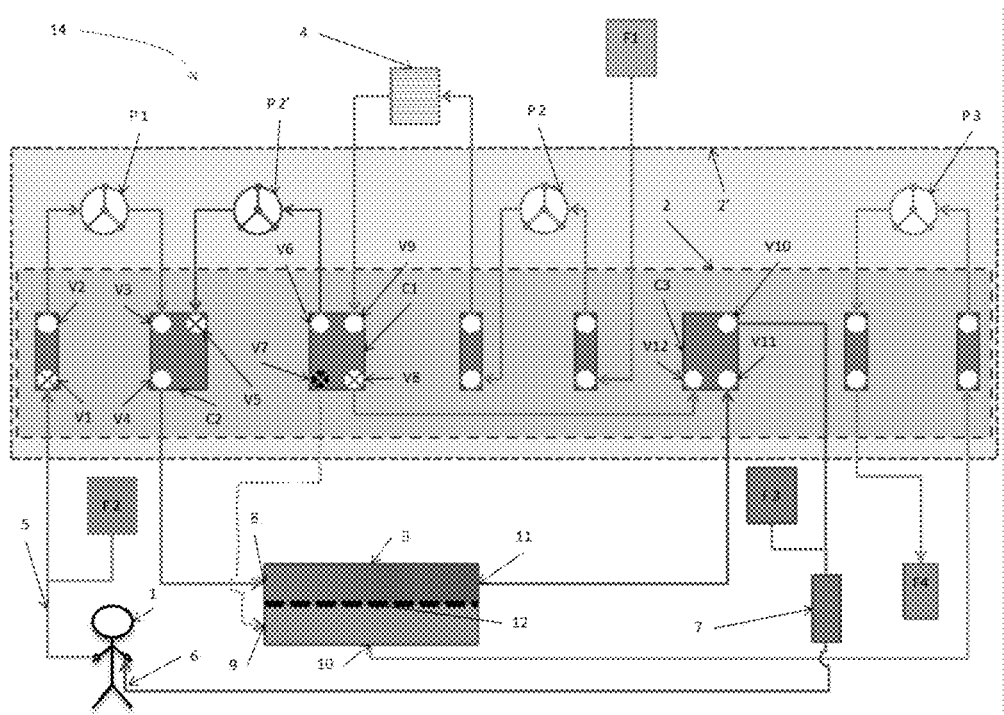
Figure 4:
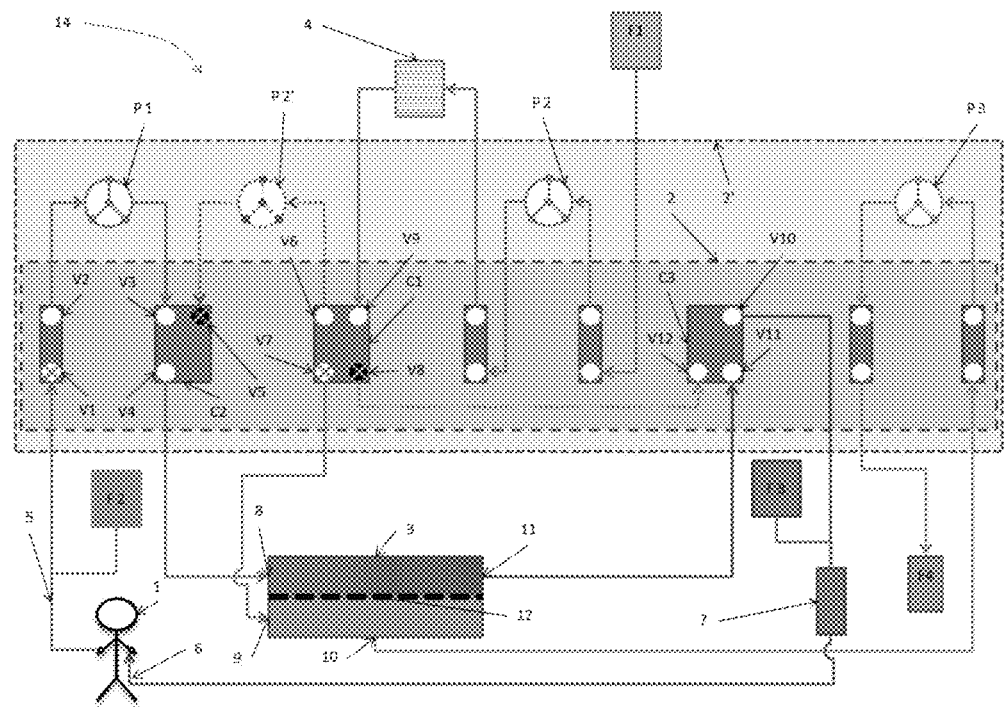
Figure 5:
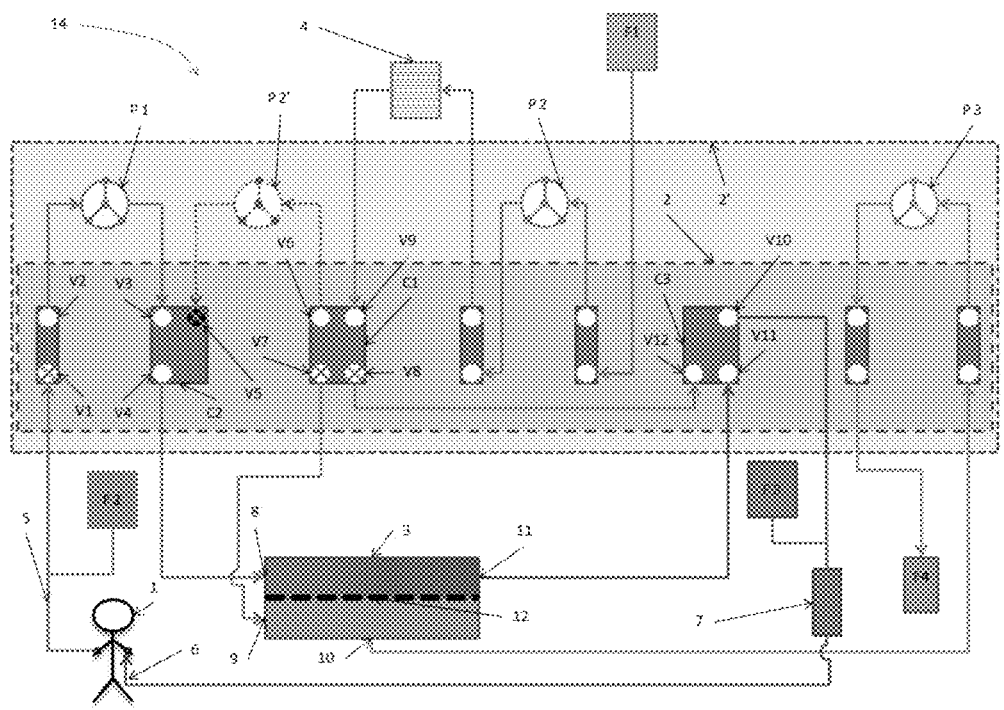
Figure 5:
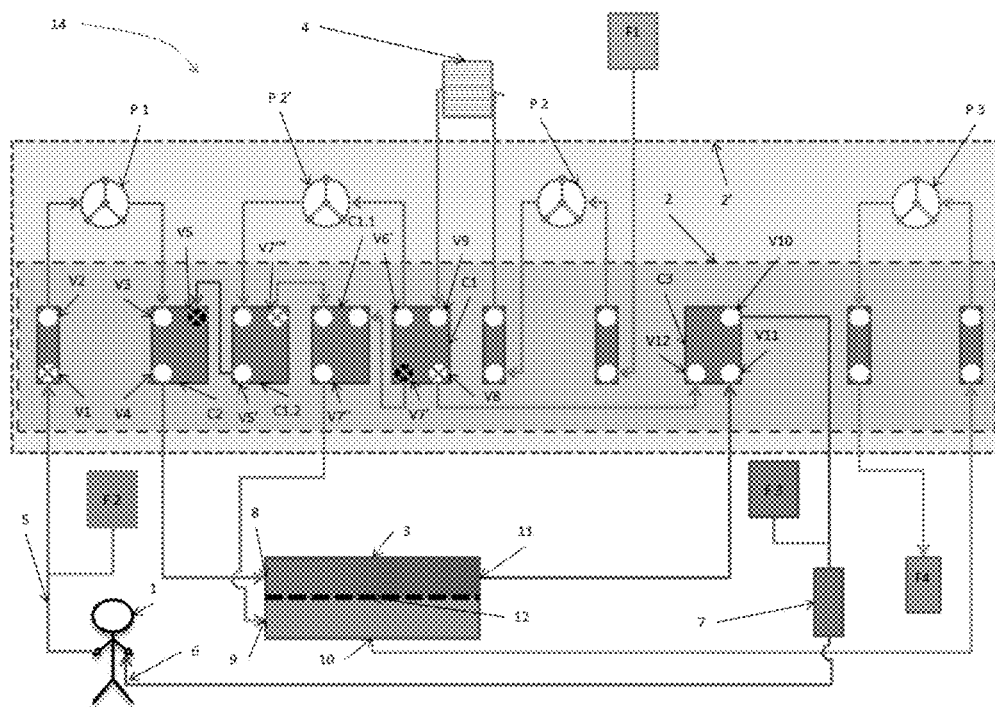
Figure 6:
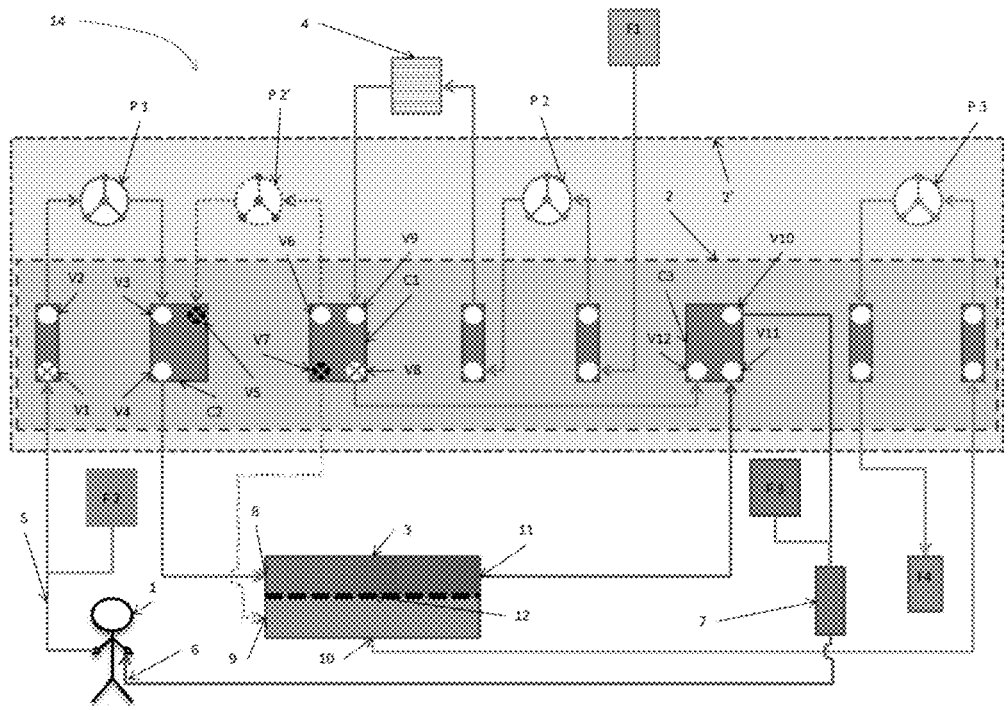
Figure 7:
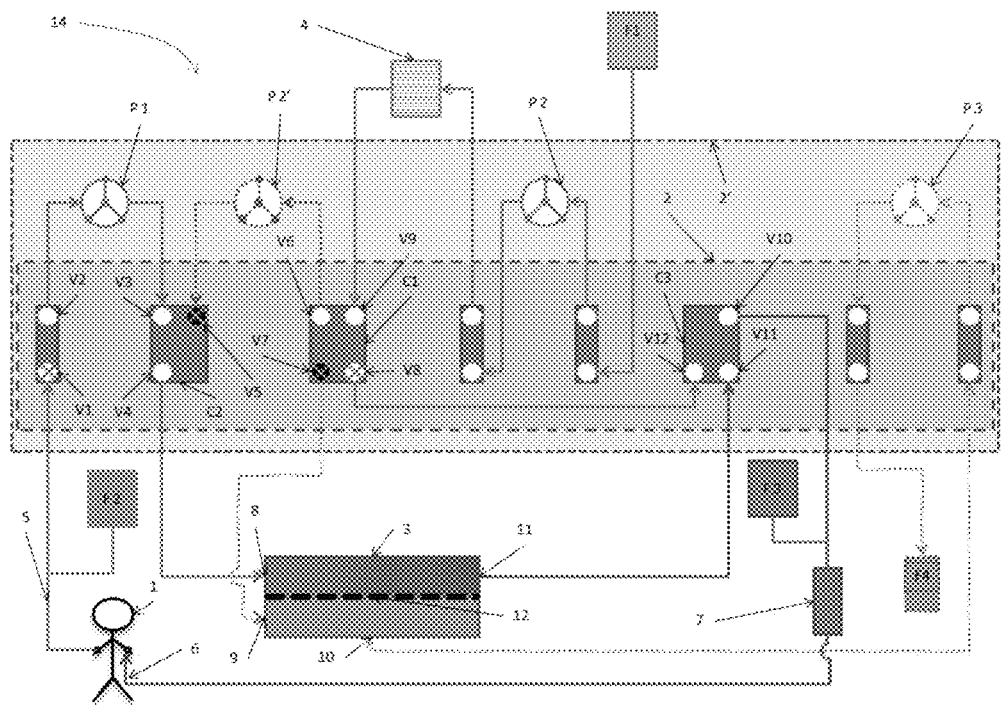
Figures 8, 9:
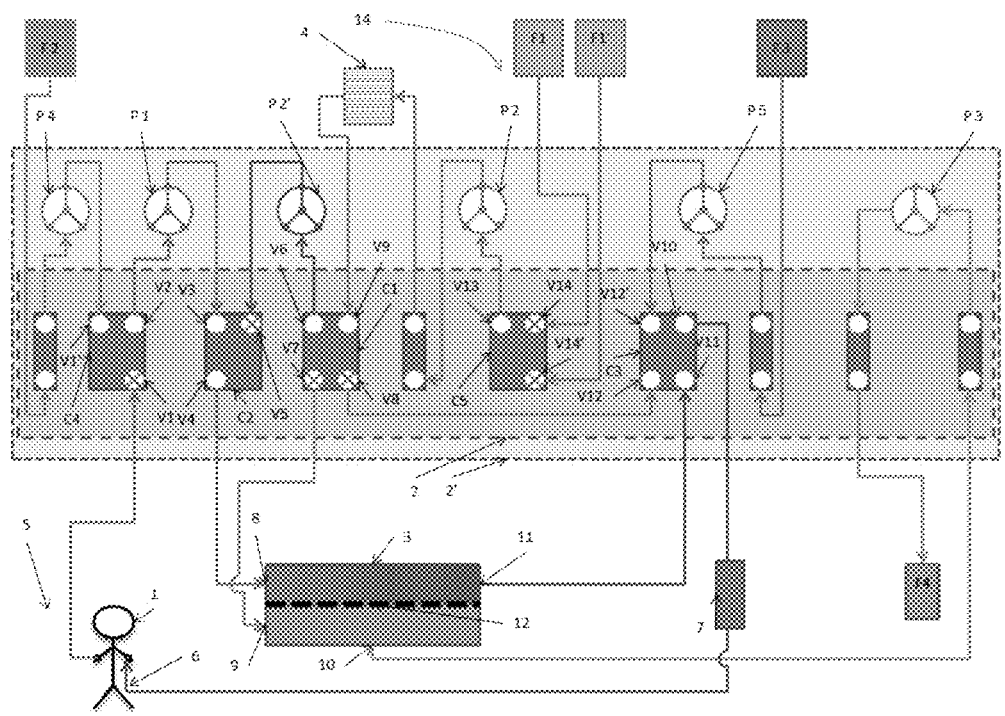
Figure 10:
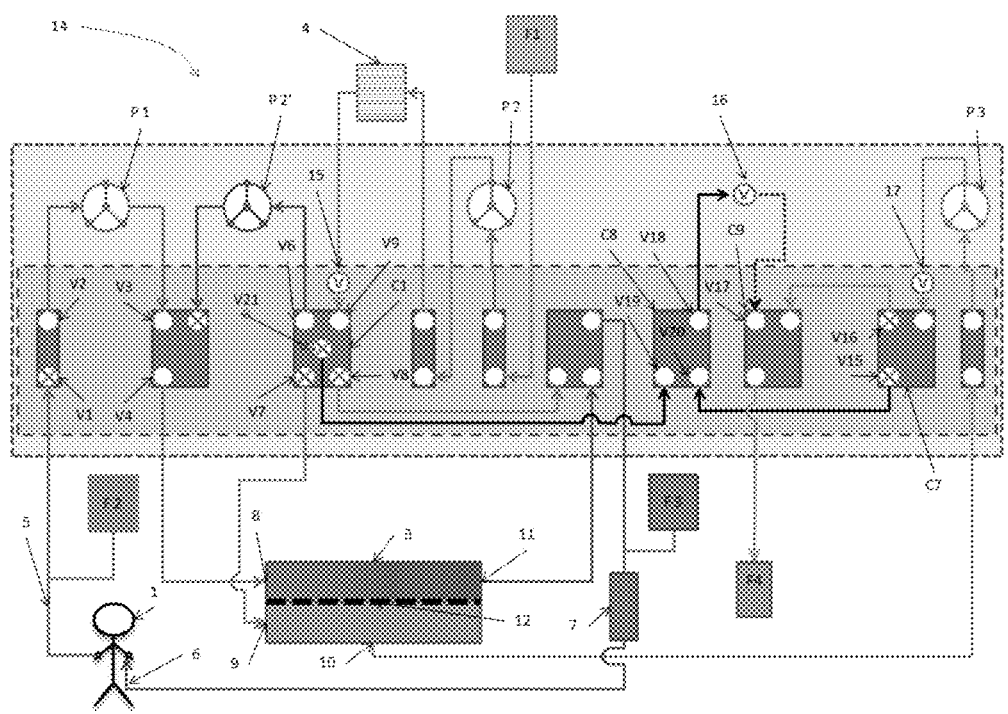
Figure 11:
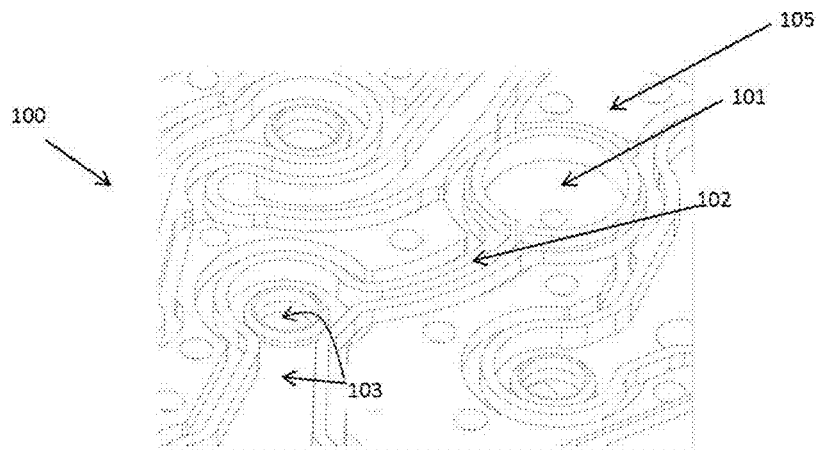
Figure 12:
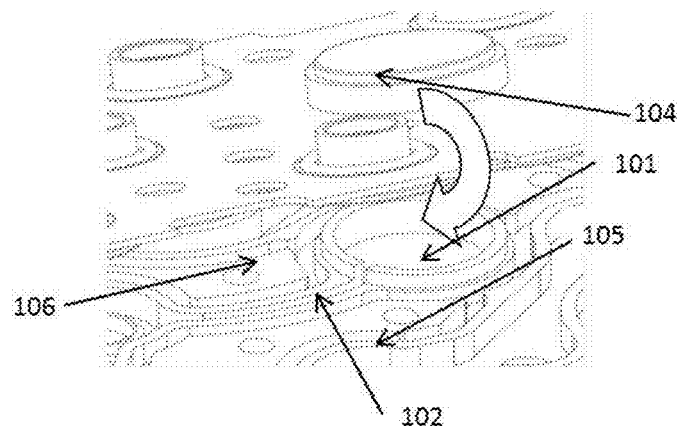
Figure 13:
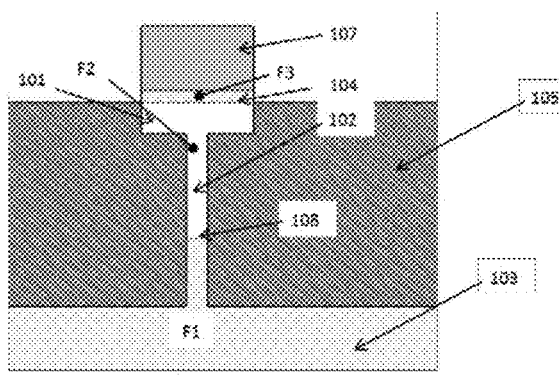
Figure 13:
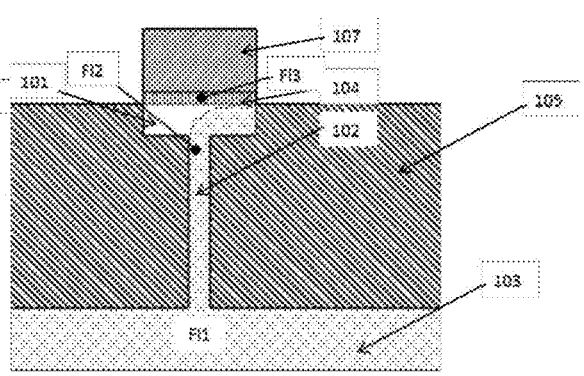
Figure 14:
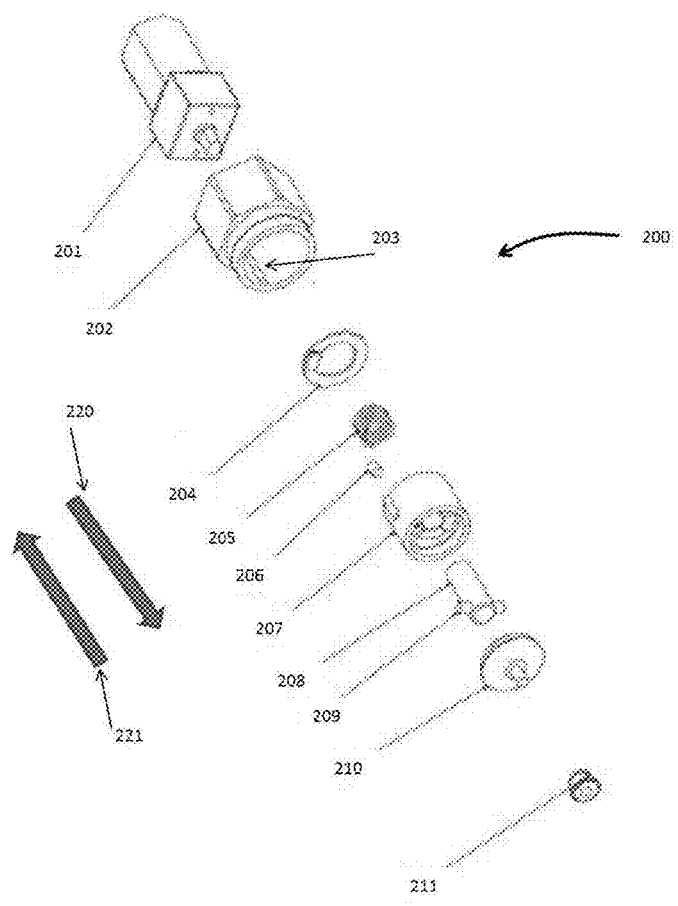
Figure 15:
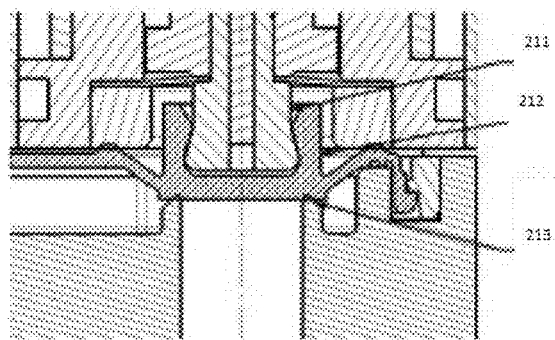
Figure 16:
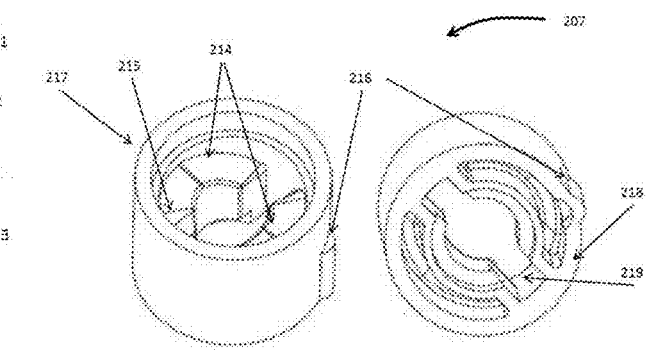
Figure 17:
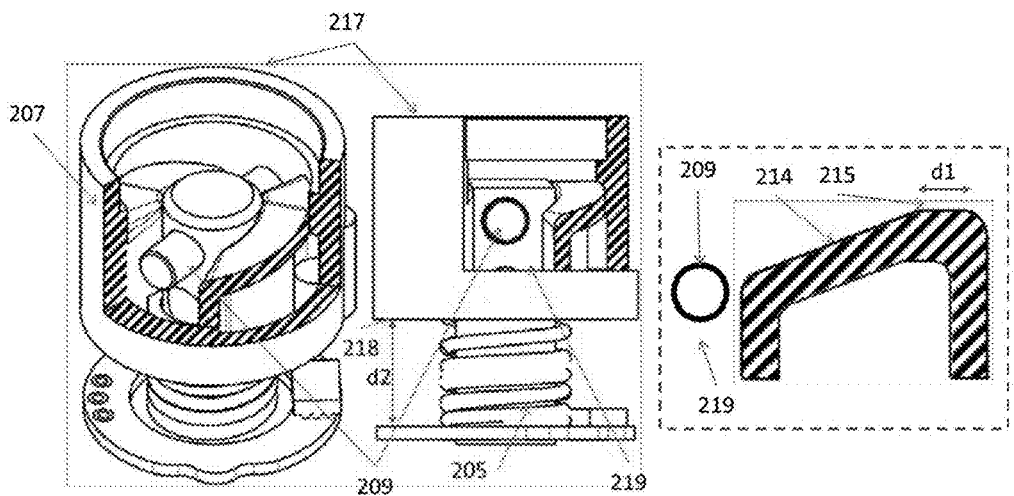
Figure 18:
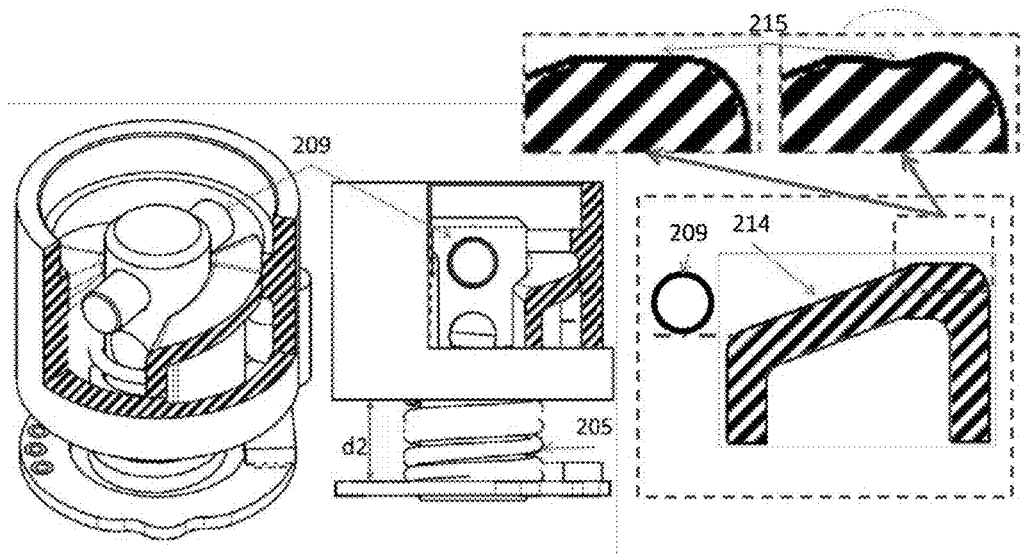
Figure 19:
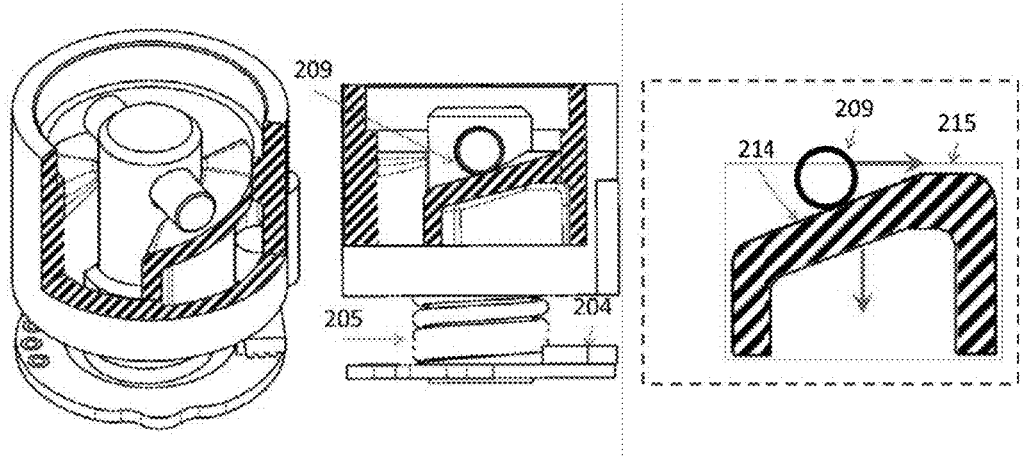
Figure 20:
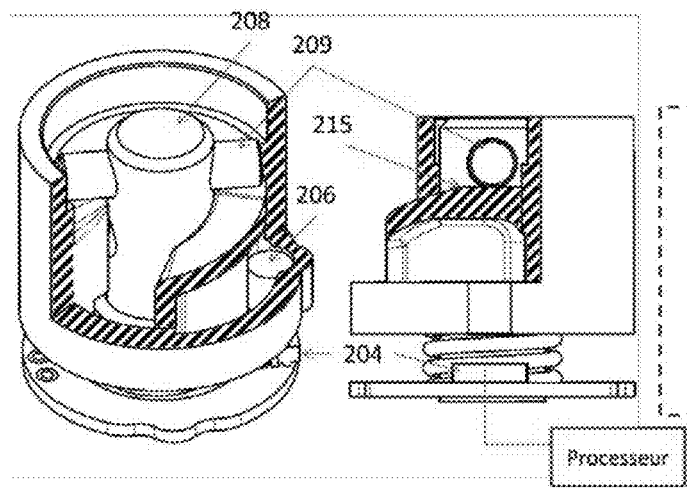
Figure 20:
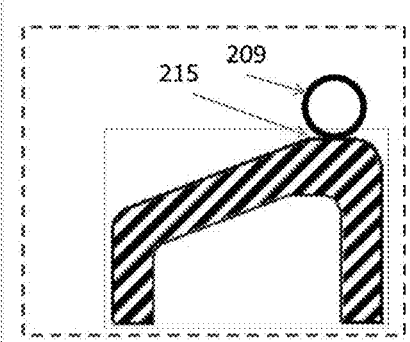
Figure 21:
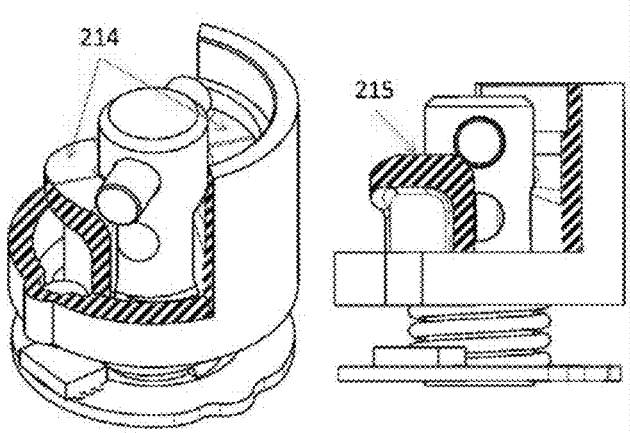
Figure 21:
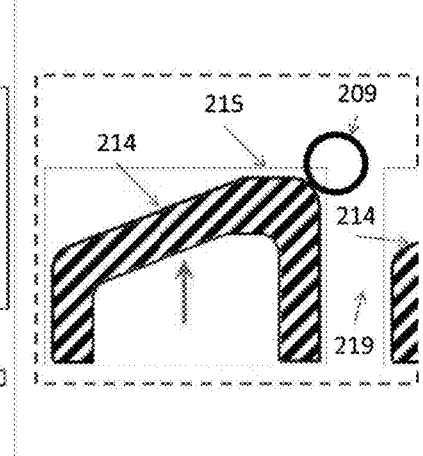
Figure 22:
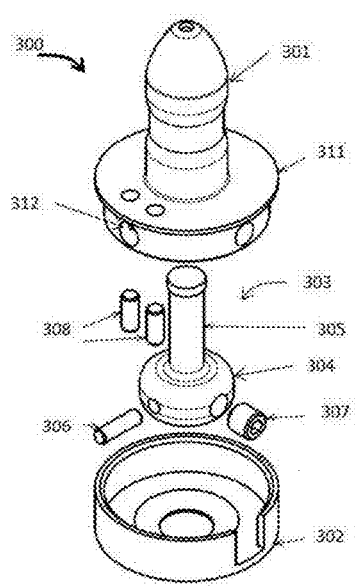
Figure 23:
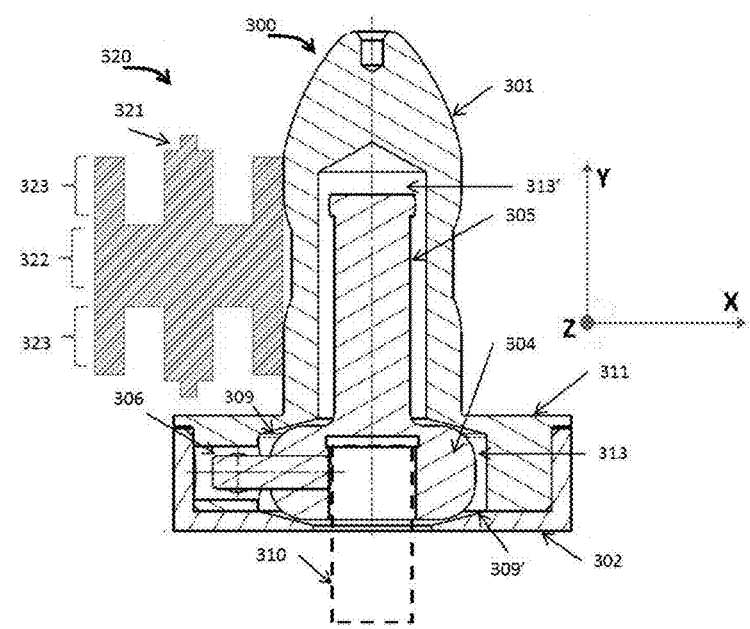
Figure 24:
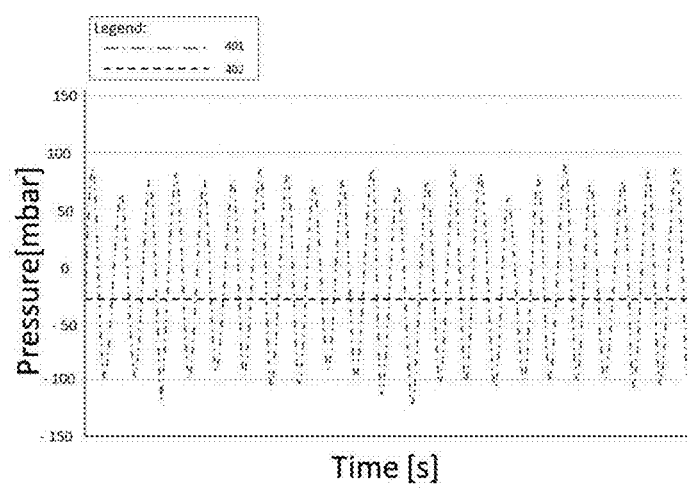
Figure 25:
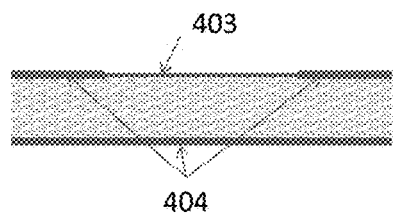
Figure 26:
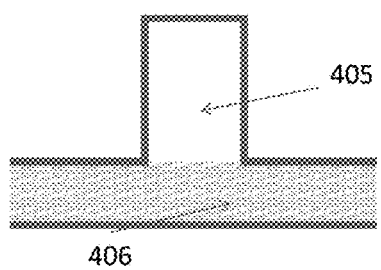
Figure 27:
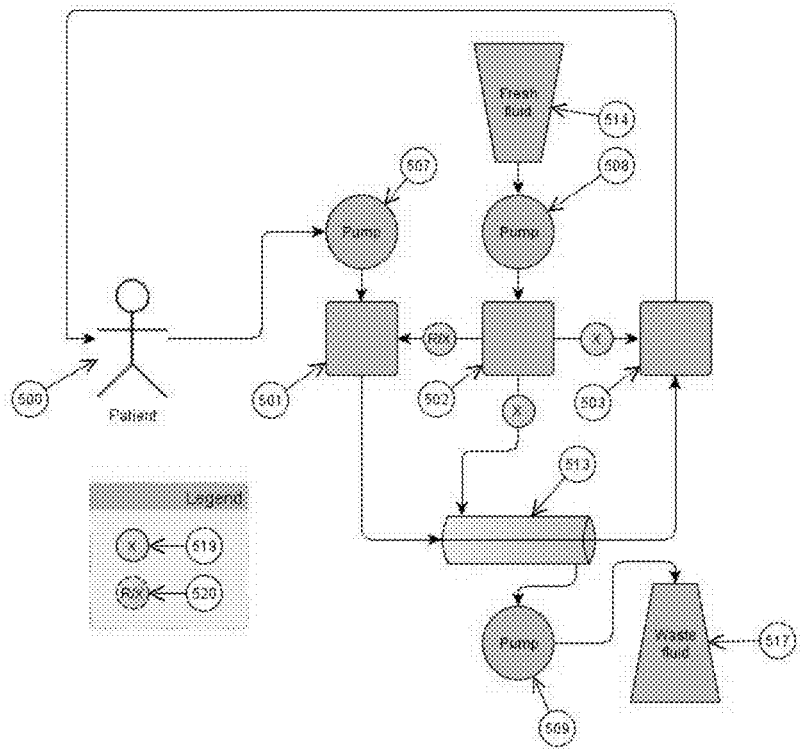
Figure 28:
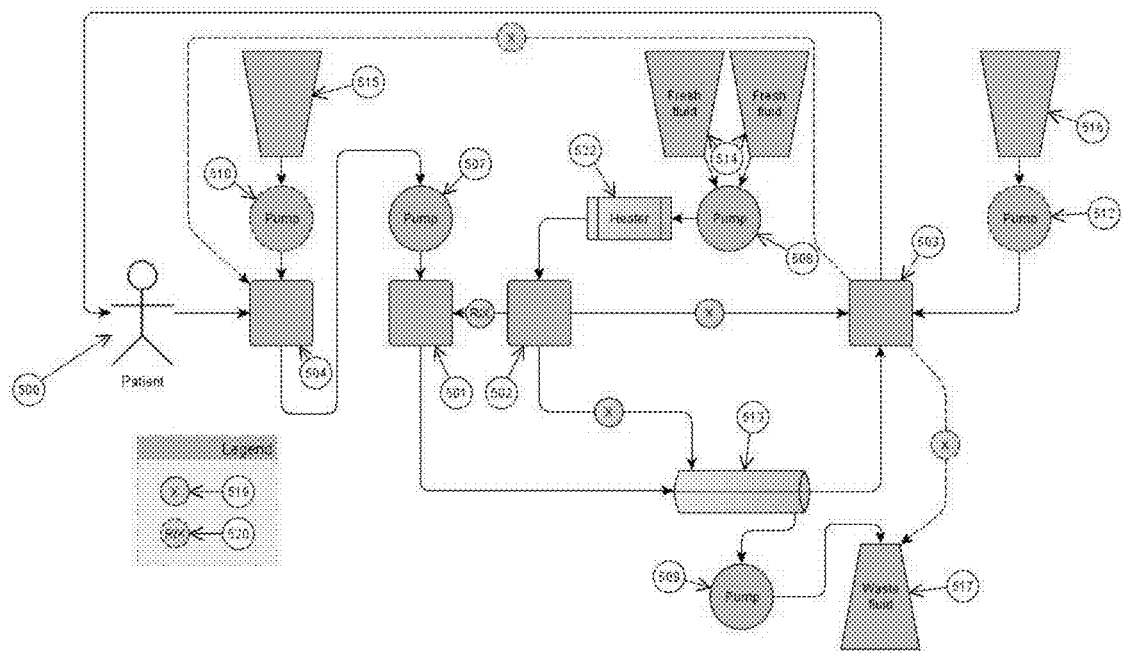
Figure 29:
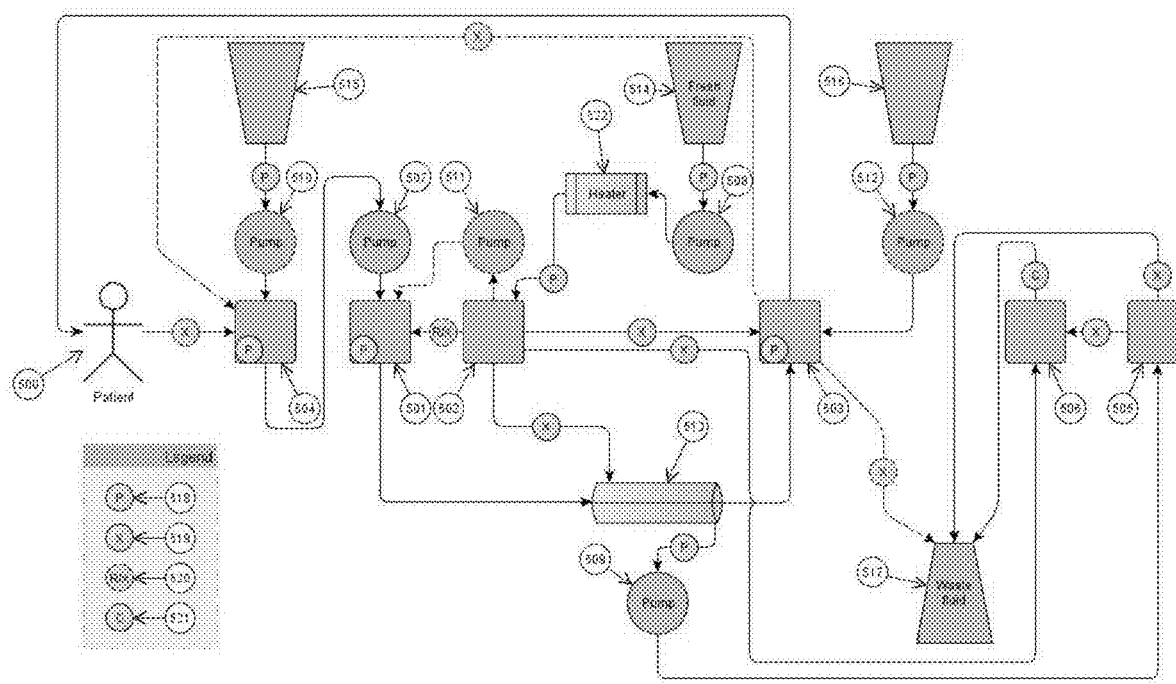
Figure 30:
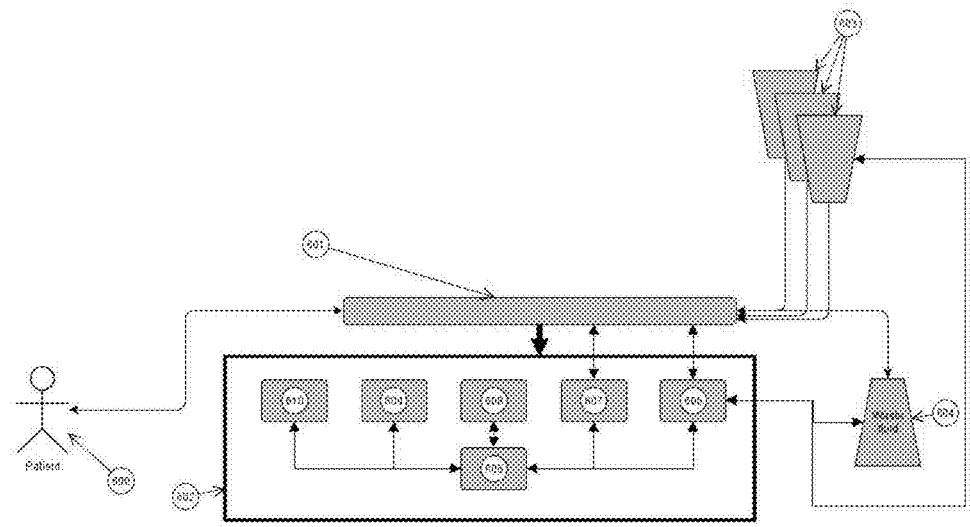
Figure 31:
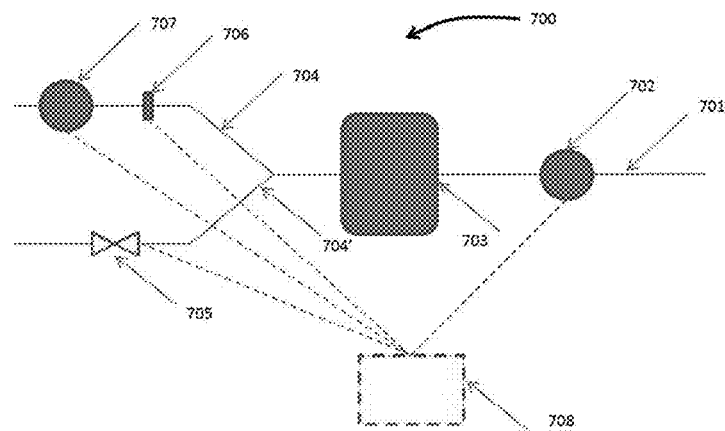
Figure 32:
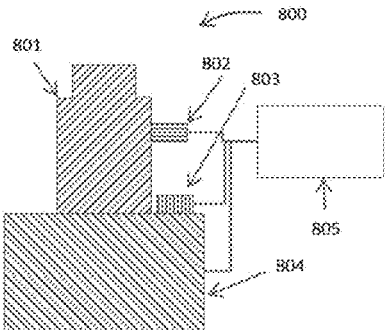
Figure 32:
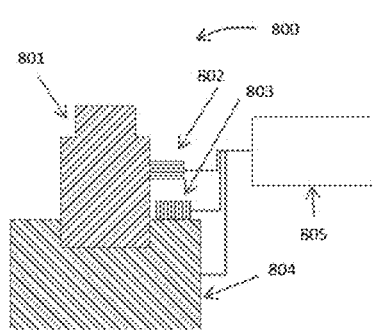
Figure 33:
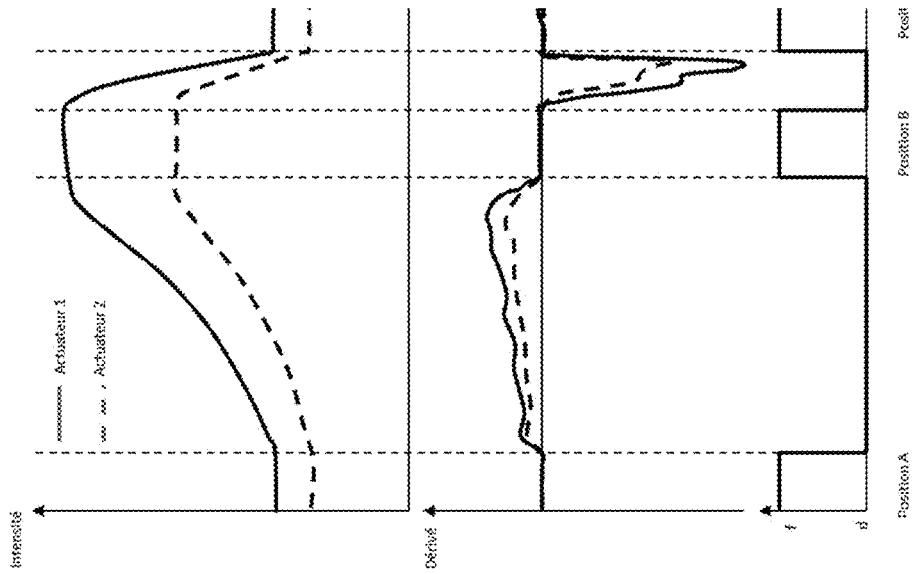

FIG. 1 schematically depicts the blood treatment system disclosed by the invention, FIG. 2 schematically depicts the use of the cassette applying a treatment of slow continuous ultrafiltration, FIG. 3 schematically depicts the use of the cassette applying a treatment of continuous venovenous hemofiltration, FIG. 4 schematically depicts the use of the cassette applying a treatment of continuous venovenous hemodialysis, FIG. 5 schematically depicts the use of the cassette applying a treatment of continuous venovenous hemodiafiltration, FIG. 5' schematically depicts another embodiment of the cassette, FIG. 6 schematically depicts the use of the cassette applying a treatment of plasma replacement, FIG. 7 schematically depicts the use of the cassette applying a treatment of hemoperfusion, FIG. 8 schematically depicts the system with several liquid supply means, FIG. 9 schematically depicts the system with a recirculation of the second flow path and reject, FIG. 10 schematically depicts the system with the reference sensor, FIG. 11 shows the rigid body of the cassette comprising a flow path and its channel for pressure measurement, FIG. 12 shows the body of the cassette and the membrane that covers the measuring zone, FIGS. 13 and 13' schematically depict the placement of the sensor offset from a flow path, FIG. 14 shows an exploded view of the linear actuator, FIG. 15 shows a sectional view in which the valve is coupled to the stub/piston, FIG. 16 shows two detailed views of the piston, FIG. 17 shows two partially cutaway views of the piston in a third position, valve (not shown) not coupled, FIG. 18 shows two partially cutaway views of the piston in a first position, valve coupled (not shown), FIG. 19 shows two partially cutaway views of the piston moving from the first position to the second position, valve coupled (not shown), FIG. 20 shows the piston in a second position, valve coupled (not shown), FIG. 21 shows the piston in a second position passing instantaneously to the first position, valve coupled (not shown), FIGS. 17', 18', 19', 20' and 21' illustrate the cooperation between the ramp and the bearing means driven by the motor (not shown), FIG. 22 shows an exploded view of the drive device of the peristaltic pump, FIG. 23 shows a sectional view of the drive device of the peristaltic pump, FIG. 24 shows a graph of the pressure peaks caused by a pump, FIGS. 25 and 26 show two different configurations of the shock-absorbing system, FIG. 27 schematically depicts a minimal embodiment of the blood treatment system, FIGS. 28 and 29 schematically depict more complex embodiments of the blood treatment system, FIG. 30 illustrates a treatment system, FIG. 31 schematically depicts the use of the additional pump for distribution of the fluid, FIGS. 32 and 32' illustrate the use of a linear actuator, FIG. 33 shows 3 graphs used by a system for actuator control.

REFERENCE NUMBERS USED IN THE FIGURES 1 patient
2 cassette
2' cassette comprising the pumps
3 blood filtration means
4 heating means
5 outlet tube from the patient
6 inlet tube to the patient
7 safety element
8 entry of the blood into the filter
9 entry of the dialysate into the filter
10 exit of the filtrate from the filter
11 exit of the blood from the filter
12 membrane of the filter
13 flow adjuster
14 blood treatment system
15 volume sensor of the third flow path
16 reference volume sensor
17 volume sensor of the first flow path
100 fluid distribution system
101 measuring zone
102 channel
103 flow path
104 membrane
105 rigid body of the cassette
106 opening
107 pressure sensor
108 hydrophobic filter
200 linear actuator
201 DC motor with reducer
202 rigid envelope
203 groove in the rigid envelope
204 sensor
205 compression means
206 magnet
207 piston
208 shaft of the motor
209 transverse shaft
210 element connecting the piston to the stub
211 stub
212 valve
213 valve seat
214 ramp
215 threshold at the summit of the ramp
216 guide means
217 distal end of the piston
218 proximal end of the piston
219 passage
220 direction 1
221 direction 2
300 drive device
301 floating shaft
302 cover
303 drive means
304 body of the drive means
305 longitudinal shaft
306 perpendicular shaft
307 fastening screw
308 hard elements
309 and 309' inner walls of the cavity
310 rotor/motor
311 base
312 cooperation element
313 cavity
313' second cavity
320 roller
321 shaft of the roller
322 rigid part
323 flexible part
401 pressure curve
402 mean pressure curve
403 flexible membrane
404 wall of the flow path
405 compressible fluid (example gas)
406 fluid
500 patient
501 1st chamber
502 2nd chamber
503 3rd chamber
504 4th chamber
505 5th chamber
506 6th chamber
507 1st pump
508 2nd pump
509 3rd pump
510 4th pump (optional)
511 5th pump (optional)
512 6th pump (optional)
513 filter
514 1st fluid supply means
515 2nd fluid supply means
516 3rd fluid supply means
517 fluid recovery means
518 pressure sensor
519 closure means (for example valve)

520 flow-limiting means or closure means
521 sensor
522 heating means
600 patient
601 cassette
602 dialysis apparatus/casing
603 fluid supply means
604 fluid recovery means
605 processor
606 sensors
607 actuators (pump, valve, etc.)
608 screen
609 acquisition means and/or other, for example power supply means
610 memory
700 fluid distribution system
701 main flow path
702 precision pump
703 flexible bag (for example flexible heating bag)
704 and 704' secondary flow path
705 valve
706 pressure sensor
707 additional pump
708 processor
800 control system
801 movable part of the actuator
802 element 1 of the sensor
803 element 2 of the sensor
804 stationary part of the actuator
805 control element (processor and/or other element)
C1 first distribution chamber
C1.1 supplementary connection chamber
C1.2 supplementary distribution chamber
C2 first connection chamber
C3 second connection chamber
C4 third connection chamber
C5 fourth connection chamber
C6 fifth connection chamber
C7 second distribution chamber
C8 sixth connection chamber
C9 seventh connection chamber
F1 first liquid supply means
F2 second liquid supply means
F3 third liquid supply means
F4 filtrate recovery means
F5 blood recovery or sampling means
F11 fluid 1
F12 fluid 2
F13 fluid 3
P1 pump of the second flow path (blood)
P2 main pump of the third flow path (dialysate or substitution)
P2' additional pump of the third flow path
P3 pump of the first flow path (filtrate)
P4 pump of the second liquid supply means
P5 pump of the third liquid supply means
V1 inlet channel for blood in the third connection chamber
V1' inlet channel of the second liquid supply means in the third connection chamber
V1" inlet channel for blood in the third connection chamber originating from the second connection chamber
V2 outlet channel for blood in the third connection chamber
V3 inlet channel for blood in the first connection chamber
V4 outlet channel for blood in the first connection chamber
V5 inlet channel for dialysate or substitution product (pre-dilution) in the first connection chamber
V5' outlet channel for dialysate or substitution product (pre-dilution) of the supplementary distribution chamber (C1.2) to the first connection chamber
V6 outlet channel for dialysate or substitution product (pre-dilution) from the first distribution chamber to the first connection chamber
V6' outlet channel for dialysate or substitution product from the first distribution chamber to the supplementary distribution chamber (C1.2)
V7 outlet channel for dialysate or substitution product from the first distribution chamber to the filter
V7' outlet channel for dialysate or substitution product from the first distribution chamber to the supplementary connection chamber (C1.1)
V7" outlet channel for dialysate or substitution product from the supplementary connection chamber (C1.1) to the filter
V7''' outlet channel for dialysate or substitution product from the supplementary distribution chamber (C1.2) to the supplementary connection chamber (C1.1)
V8 outlet channel for dialysate or substitution product (post-dilution) from the first distribution chamber to the second connection chamber
V9 inlet channel for dialysate or substitution product in the first distribution chamber
V10 outlet channel for blood to the patient
V10' outlet channel for blood to the third connection chamber
V10" outlet channel for blood to a recovery means
V11 outlet channel for blood in the second connection chamber originating from the filter
V12 inlet channel for dialysate or substitution product (post-dilution) originating from the first distribution chamber
V12' inlet channel of the third liquid supply means into the second connection chamber
V13 outlet channel for dialysate or substitution product
V14 and V14' inlet channel for dialysate or substitution product of the first supply means
V15 outlet channel for filtrate from the second distribution chamber to the sixth connection chamber
V16 outlet channel for filtrate from the second distribution chamber to the seventh connection chamber
V17 inlet channel to the seventh connection chamber originating from the reference volume sensor
V18 outlet channel for the volume to be measured
V19 inlet channel in the sixth connection chamber for the volume to be measured (dialysate)
V20 inlet channel in the sixth connection chamber for the volume to be measured (filtrate)

DETAILED DESCRIPTION OF THE INVENTION

In the present document, the detailed description of the invention includes embodiments of devices, systems and methods that are presented by way of illustration. It will be appreciated that other embodiments are conceivable and may be applied without departing from the scope or spirit of the invention. Therefore, the detailed description given below must not be taken in a restrictive sense.

Unless otherwise indicated, the scientific and technical terms used in the present document have meanings currently used by a person skilled in the art. The definitions given in this document are mentioned in order to facilitate an understanding of the terms frequently used and are not intended to limit the scope of the invention.

The indications of direction used in the description and in the claims, such as "up", "down", "left", "right", "upper", "lower", and other directions or orientations are mentioned in order to afford greater clarity with reference to the figures. These indications are not intended to limit the scope of the invention.

In the present document, the verbs "have", "comprise", "include" or equivalent are used in a broad sense, generally signifying "including but not limited to".

The word "or" is generally employed in a broad sense covering "and/or" unless the context clearly indicates the contrary.

In the present invention, a channel can be defined as being a flow conduit of hollow and elongate shape allowing the passage of a liquid and/or of a gas from one location to another. It can take the form of a flexible tube or tubing or of a cavity inside a cassette. Some channels have valves that can be actuated preferably by means of a linear actuator governed by a controller in order to close or open the channel. Without actuation, said valves are preferably closed. A chamber can be a cavity or a channel having several inlets and/or outlets or can take the form of a simple intersection of two channels. Each chamber has an inlet called inlet channel and an outlet called outlet channel.

Principle of the Invention Concerning a Blood Treatment System

The embodiment shown schematically in FIG. 27 is a simplified embodiment. The treatment system comprises three pumps (507, 508, 509), three flow paths and a filtration means or filter (513). The first flow path starts from the filtering means (513) and reaches to the reservoir (517), also called the fluid recovery means. The fluid flowing through the first flow path is called the filtrate. The second flow path starts from the patient, passes through the filter (513) and returns to the patient (500). The fluid flowing through the second flow path is the blood of the patient. The third flow path is supplied with a fluid generally called dialysate (although the invention is not limited to this fluid) which flows from the first liquid supply means, likewise called dialysate reservoir (514). The dialysate initially flows through the third flow path, after which it flows into one or more secondary flow paths (in diluted form or transformed). The dialysate (or other fluid of the third flow path) can: mix with the blood:
  before the filter (513) in order to effect a pre-dilution, and/or
  after the filter (513) in order to effect a post-dilution, and/or
  supply the filter (513).

In order to permit these different solutions and thereby perform any treatment technique by dialysis, the system requires three chambers (501, 502, 503). The second chamber (502), also called distribution chamber, makes it possible to direct the dialysate toward the filter (513), the first chamber (501) in order to effect a pre-dilution and/or the second chamber (502) to effect a post-dilution. The first and third chambers (501, 503) can also be called connection chamber. The first and third chambers (501, 503) make it possible to mix the blood with the dialysate, in other words the first and third chambers (501, 503) allow the fluid of the third flow path to flow into the second flow path. The channels connecting the chambers to each other or to the filter can comprise valves (519) and/or a flow-restricting or closure means (520).

FIG. 28 schematically depicts a more complex system with the addition of further optional elements. These can be, for example:
A new supply system (515) that can contain, for example, an anticoagulant. This fluid can be contained in a reservoir (515) and delivered by a pump (510) or by gravity. This supply means can be a syringe and/or
Another supply means (516) that can contain, for example, an agent inhibiting the anticoagulant. This fluid can be contained in a reservoir (516) and delivered by a pump (512) or by gravity. This supply means can be a syringe, and/or
A new channel for connecting the third chamber (503) (that normally used for the post-dilution), or another chamber (located downstream of the third chamber), to the first chamber (501) (that normally used for the pre-dilution), or to another chamber (504) (located upstream of the first chamber), this new channel preferably comprising a valve controlled by a controller. It allows the fluid contained in the second flow path to circulate in a loop so as not to stagnate in the channels, and/or
Another channel for connecting the third chamber (503) to the fluid recovery means (517). This channel preferably comprises a valve. It can permit, for example, the priming of the system or the disposal of some of the fluid flowing in the second flow path, and/or
A heating means (522)

Another embodiment is disclosed by FIG. 29. This embodiment can comprise at least one pressure sensor (518), located in or near the chambers (504, 501, 502, 503), the filter (513) and/or the supply means (515, 516, 514), and/or an additional pump (511) (in place of the flow limiter (520)) in the third flow path between the distribution chamber (502) and the connection chamber (501). The system can additionally comprise a calibration system that can comprise a sensor common to the first and third flow paths. This calibration system comprises two supplementary channels that allow the fluids contained in the first and third flow paths to flow toward a sixth chamber (506). This sixth chamber (506) comprises or has connected to it a sensor permitting the calibration of elements (sensors and/or pump) of the first and third chambers such that it is calibrated identically.

FIG. 30 discloses a treatment system as described above. This system additionally comprises a cassette (601) permitting the functions of distribution of fluids. This cassette (601) is connected to reservoirs (603, 604) and cooperates with a device (602). The device (602), called dialysis apparatus, can be reusable, while the cassette (601) can be disposable. The device (602) can comprise a processor (605), at least one sensor (606) designed to cooperate with the cassette (601), at least one actuator (607) (for example pump or control means) designed to cooperate with the cassette (601), a screen (608), at least one acquisition means and/or other, such as a battery (609) and/or a memory (610).

Embodiments of Cassettes According to the Operating Principle Described Above

According to FIG. 1, the invention discloses a system (14) with which it is possible to carry out treatment of a patient's blood and which comprises a blood filtration means (3), at least one liquid supply means (F1), two patient tubes, namely an outlet tube (5) for collecting the blood to be treated and an inlet tube (6) for re-injecting the treated blood into said patient, a filtrate recovery means (F4), at least three fluid pumps (P1, P2, P3), a cassette (2, 2') composed of channels and valves for directing the fluids. Said cassette (2, 2') comprises at least one distribution chamber (C1, C1.2, C7) comprising a single inlet channel and at least two outlet channels. Said treatment system (14) comprises a controller for controlling the opening and closure of said valves depending on the desired treatment.

Said treatment system (14) additionally comprises a first flow path connecting said blood filtration means (3) to the filtrate recovery means (F4), composed of a series of channels and a dedicated pump (P3); a second flow path dedicated to the circulation of the blood, comprising a series of channels, said blood filtration means (3), said patient tubes (5, 6) and a dedicated pump (P1); a third flow path composed of a liquid supply means (F1), at least one dedicated pump (P2), a series of channels, a heating means (4) and at least one distribution chamber (C1, C1.2).

Advantageously, said distribution chamber (C1) comprises at least three (separate) outlet channels connected directly or indirectly
- to the second flow path upstream of said blood filtration means (3),
- to the second flow path downstream of said blood filtration mans (3),
- to said blood filtration means (3).

Said cassette can additionally comprise a flow regulator designed to govern the amount of liquid of the third flow path flowing into at least one of said outlet channels of said distribution chamber (C1). Moreover, said at least one flow regulator is controlled by said controller, which can comprise the processor (605).

Said cassette (2') can likewise contain the pumps and/or other elements.

The treatment system additionally comprises, in the third flow path, a flow adjuster (13, P2') located between said distribution chamber (C1) and said first connection chamber (C2).

In one embodiment, the third flow path has an additional pump (P2') in the third flow path, located between the distribution chamber (C1) and said first connection chamber (C2). Said additional pump (P2') has the complete or partial role of flow adjuster. The aim of the flow adjuster is to control the flow of the fluid passing from the distribution chamber (C1) to the connection chamber (C2). The adjuster thus makes it possible to distribute the quantity of fluid in the connection chamber (C2) and at least one other connection chamber or the blood filtration means (3).

In one embodiment, one or more flow adjusters (also called flow restrictors) can be placed between any chamber or element (for example blood filtration means (3)). A flow adjuster (13) can be a pump, a proportional valve and/or a set of channels with dedicated valve and different diameters, etc. A supplementary safety valve can be added upstream or downstream of the flow adjuster (13-520). A flow adjuster permits a 0% to 100% flow of the fluid, at one moment or during a given period, through said flow means. In other words, the flow of a fluid coming from at least one liquid supply means can be distributed between the different channels according to the requirements of the treatment.

In one embodiment, the treatment system (14) comprises a second liquid supply means (F2-515) located on the patient outlet tube (5) or in the cassette (2, 2'-601). Said second supply means can contain an anticoagulant such as citrate, heparin, danaparoid sodium or similar.

In one embodiment, said system (14) comprises a third liquid supply means (F3-516) located on the patient inlet tube (6) or in the cassette (2, 2'-601). Said liquid supply means can contain calcium or an agent inhibiting the anticoagulant.

On the patient inlet tube (6) and/or in the cassette (2, 2'-601), the system comprises at least one safety element (7) for detecting air bubbles in the second flow path and/or for stopping the circulation of the blood and/or a means for capturing said air bubbles.

Location of the Heating Means and/or use of Two Pumps in the Third Flow Path:

According to the operating principle disclosed by FIG. 31, in order to be effective, the fluid distribution system (whether for a cassette as described in the present document or for another distribution system) can comprise a precision pump (702), a fluid supply means, a flexible bag (703) and an additional distribution pump (707). The system additionally comprises a main flow path (701) which divides into at least two secondary and separate flow paths (704, 704'). The precision pump (702) and the flexible bag (703) are positioned in the main flow path (701), the flexible bag being positioned downstream of said pump. Thus, all the pumped fluid is known with precision and can at least in part be stored at least temporarily in the flexible bag. The additional pump (707) is positioned in one of the secondary flow paths (704). Preferably, the other secondary flow path (704') comprises a valve (705). In one embodiment, at least one flow path comprises a pressure sensor (706) positioned downstream of the precision pump (702). Preferably, said pressure sensor (706) is positioned in the secondary flow path (704), which comprises the additional pump (707), and upstream of the additional pump. The flexible bag (703) is preferably a heating means.

Given that some techniques of continuous renal replacement therapy require heating the dialysate and/or substitution liquid during its injection, said heating means (4) can be located at various locations of the third flow path. In one embodiment, the cassette has a heating means (4) inside the distribution chamber (C1) or upstream of the latter.

In one embodiment according to the principle described above, the heating means (4) is a flexible bag located between the main pump (P2) of said third flow path and said distribution chamber (C1), which makes it possible to create a constant positive pressure in said bag (4). The heating means is supplied continuously by the pump (P2), which makes it possible, among other things, to guarantee proper control of the reheating of the liquid of the third flow path. Said bag (4) is then directly connected to the inlet channel (V9) of the distribution chamber (C1).

As a result of this configuration, all the injected liquid passes through a single pump (P2). The pre-dilution pump (P2') (also called additional pump) only distributes the liquid before and/or after the filter. Thus, a single precision pump is necessary. The pump (P2) is the precision pump and allows the quantity of pumped fluid to be known. The additional pump simply permits distribution between the pre-dilution (before the filter) and the post-dilution (after the filter). The use of the pumps is as follows:
- If only post-dilution is programmed: the pre-dilution pump (P2') is stopped and all the liquid will be injected after the filter (3). The post-dilution valve (V8) is opened. The pre-dilution valve (V5) is preferably closed.
- If only pre-dilution is programmed: the post-dilution pump (P2) delivers the substitution volume. The post-dilution valve (V8) prevents passage of the liquid after the filter. The pre-dilution pump (P2') also makes it possible to regulate the fluid so as to avoid the pressure in the heating means (4) becoming negative.
- If pre-dilution and post-dilution are programmed: the main pump (P2) delivers all the substitution volume required (pre and post). The post-dilution valve (V8) is opened. The pre-dilution pump (P2') taps some of the liquid in order to inject it before the filter (3). If there is an error of precision in the distribution before and after injection, its seriousness is limited because the volume is in any case injected into the patient.

Use of the Cassette Depending on the Various Treatments:

Slow continuous ultrafiltration (SCUF): FIG. 2 shows the use of the cassette applying a treatment of slow continuous ultrafiltration. This technique is used to eliminate excess liquid by means of the convection principle.

Thus, the controller opens only the valve V1 of the second flow path and closes the valves V5, V7 and V8 of the third flow path. The pumps P1 and P3 then function, while P2 and P2' do not function.

Continuous venovenous hemofiltration (CVVH): FIG. 3 shows the use of the cassette applying a treatment of continuous venovenous hemofiltration. This technique is used to obtain the removal of dissolved substances by means of the convection principle. A substitution solution is injected into the circuit before (pre-dilution) and/or after (post-dilution) the filtration means (3).

Thus, the controller opens the valves V1 of the second flow path and V5 and/or V8 of the third flow path, and the valve V7 is closed. The pumps P1, P2 (optionally P2') and P3 function.

Continuous venovenous hemodialysis (CVVHD): FIG. 4 shows the use of the cassette applying a continuous venovenous hemodialysis treatment. This technique is used to obtain the removal of dissolved substances (small molecules: urea, creatinine, K, etc.) and to obtain a water equilibrium by the diffusion principle. The dialysate is injected into the filtration means (3).

Thus, the controller opens the valves V1 of the second flow path and V7 of the third flow path, and the valves V5 and V8 remain closed. The pumps P1, P2 and P3 function.

Continuous venovenous hemodiafiltration (CVVHDF): FIG. 5 shows the use of the cassette applying a treatment of continuous venovenous hemodiafiltration. This technique is used to obtain the removal of dissolved substances (small or medium-sized molecules) by means of the principles of diffusion and convection. The dialysate and/or a substitution solution are injected into the filtration means (3) and into the blood after the filtration means (3).

Thus, the controller opens the valve V1 of the second flow path and also the valves V7 and V8 of the third flow path. The valve V5 remains closed. The pumps P1, P2 and P3 function. In this embodiment, the outlet channels V7 and V8 are proportional valves or another means of controlling the flow that passes through these valves.

In another embodiment, shown in FIG. 5', the cassette comprises a supplementary distribution chamber (C1.2) and a supplementary connection chamber (C1.1). Said supplementary distribution chamber (C1.2) is supplied directly by the additional pump (P2'). Said supplementary distribution chamber (C1.2) makes it possible to distribute the dialysate or substitution product either to the first connection chamber (C2) for the pre-dilution or to said supplementary connection chamber (C1.1). Said supplementary connection chamber (C1.1) is also supplied with dialysate or substitution product by the first distribution chamber (C1) by means of the outlet channel with dedicated valve (V7'). Said supplementary connection chamber (C1.1) also has an outlet channel (V7'') connecting to the filter (3). The benefit of such an arrangement is to increase the precision of the quantities injected into the filter and into the second connection chamber for the post-dilution or into the filter and into the first connection chamber for the pre-dilution. Thus, the additional pump (P2') ensures that the quantities of fluid that are to be distributed are distributed with precision. In this embodiment, for a continuous venovenous hemodiafiltration treatment, the valves V1, V8 and V7'' are opened.

Therapeutic plasma exchange (TPE): FIG. 6 shows the use of the cassette applying a therapeutic plasma exchange. This technique permits plasma exchange by membrane filtration. A substitution solution is injected in order to replace the extracted plasma.

Thus, the controller opens the valve V1 of the second flow path and also the valve V8 of the third flow path. The valves V5 and V7 remain closed. The pumps P1, P2 and P3 function. Preferably, F2 and F3 deliver their fluid in the second flow path.

Hemoperfusion: FIG. 7 shows the use of the cassette applying a treatment of hemoperfusion. This technique is used to eliminate the toxic substances from the blood of a patient, where the filtration means contains an absorbent substance. A substitution solution is injected in order to replace the extracted plasma.

Thus, the controller opens the valve V1 of the second flow path and also the valve V8 of the third flow path. The valves V5 and V7 remain closed. The pumps P1 and P2 function, while the pump P3 does not function. Preferably, F2 and F3 deliver their fluid in the second flow path.

System having Several Liquid Supply Means

When one flow path (coming, for example, from a supplementary liquid supply means) connects to another flow path, the cassette preferably comprises a connection chamber permitting the intersection of said two flow paths.

In an embodiment shown in FIG. 8, the cassette comprises:

A third connection chamber (C4) comprising an inlet channel (V1'), an inlet channel with dedicated valve (V1) and an outlet channel (V2). This connection chamber introduces a fluid, contained in a second liquid supply means (F2), into the flow path of the blood (second flow path), and said second liquid supply means (F2) preferably contains an anticoagulant agent, and/or A third inlet channel (V12') in the second connection chamber (C3). The third inlet channel (V12') allows a fluid, contained in a third liquid supply means (F3), to be injected into the flow path of the blood (second flow path), and said third liquid supply means (F3) preferably contains an agent inhibiting the anticoagulant, and/or A fourth connection chamber (C5) comprising at least two inlet channels (V14, V14') with dedicated valve, making it possible to have at least two different or similar fluids in the third flow path, for example dialysate in one bag and a substitution product in another.

Circulation without Interruption, Emptying and Priming of the Second and/or Third Flow Path:

In an embodiment shown in FIG. 9, the second connection chamber (C3) comprises:

An inlet channel (V11) of the second flow path connected to the filtration means (3)

An inlet channel (V12) of the third flow path connected to the distribution chamber (C1)

Three outlet channels with dedicated valve (V10, V10', V10''), the first being connected to the patient inlet tube (6), the second being connected to an inlet channel of the second connection chamber (C4), and the third being connected either to a recovery means (F5) or directly or indirectly to the filtrate recovery means (C6).

This embodiment permits the following, for example:

If a problem occurs, the controller can close the valve V10 in order, for example, to avoid injecting an air bubble into the patient, or another element that may endanger the patient's life. In this case, the blood remaining in the cassette and the filter risks coagulating. It is therefore imperative that the blood does not stagnate in the cassette or in the filter. Thus, P1 continues to function, collecting blood from the second connection chamber in order to circulate blood in a loop between the first and second connection chambers and the filter. V10' and/or V1" are opened, while V1, V10 and V10" are closed.

to take samples of the blood by virtue of the valve V10", to start the treatment by emptying the air from the system, to rinse the second flow path with the fluid from the third flow path, to eliminate all or some of the fluid contained in the second and/or third flow path.

Means and Method for Calibration of the Pumps and/or Sensors of the First and Third Flow Paths:

Some techniques of continuous renal replacement therapy require precise knowledge of the quantity of the volume injected and withdrawn via the third flow path and first flow path, respectively. The treatment system preferably comprises peristaltic pumps. This type of pump may have a certain imprecision. Thus, according to FIG. 10, in order to know with precision the volume quantity added or withdrawn, the distribution system comprises at least two volume sensors, which are able to measure the volumes of the third and first flow paths.

The first sensor (15) is arranged in the third flow path between the distribution chamber (C1) and the main pump (P2) and measures the injected volume coming from the first liquid supply means (F1, F1'). Preferably, the sensor (15) is located after the heating means (4). The second sensor (17) is placed in the first flow path downstream of the pump and before any other chamber. Said second sensor (17) measures the volume of the filtrate withdrawn. To avoid any risk of contamination, the two sensors are preferably located in the cassette. In a preferred embodiment, the treatment system comprises:

a third volume sensor (16) for comparing the volumes measured by the two preceding volume sensors (15, 17), said sensor also being called a reference sensor, a means of sampling the fluids coming from the first and third flow paths. Said sampling means comprises a sixth connection chamber (C8) having an outlet channel directly connected to said third sensor (16) and two inlet channels (V19, V20) connected respectively to:

an outlet channel with dedicated valve (V21) located in the first distribution chamber, an outlet channel with dedicated valve (V15) located in the second distribution chamber, optionally, a seventh connection chamber (C9) allowing the reference sensors (16) to discard the liquids measured in the filtrate recovery means (F4).

To avoid any risk of contamination, said third sensor can preferably be located in the cassette.

The method comprises the following steps:

calibration of the volume injected:

opening of the valve (V21) and closure of the other valves, actuation of the main pump (P2) of the third flow path, measurement of the volume pumped by said pump (P2) via said first sensor (15) of said third flow path, measurement of said pumped volume via the reference sensor (16), comparison of the two measurements, calibration of the first sensor (15) and/or of the pump (P2)

calibration of the volume withdrawn:

opening of the valve (V15) and closure of the other valves, actuation of the pump (P3) of the filtrate of the first flow path, measurement of the volume pumped by said pump (P3) via said second sensor (17) of said first flow path, measurement of said pumped volume via the reference sensor (16), comparison of the two measurements, calibration of the first sensor (15) and/or of the pump (P2).

These steps can be performed at the time of priming and/or during the treatment.

The first and second sensors (15, 17) are set to a common sensor called reference sensor (16) for relative optimum precision. Said sensors, although inexact, are sufficiently effective, since they are (relatively) exact in comparison with the reference sensor (16).

Said reference sensor (16) can be a balance, a volumetric pump, a mass flow sensor or any sensor by which a volume can be measured or deduced.

Preferably, said first and second sensors (15, 17) continuously measure the liquids passing through the third and first flow paths, respectively. By means of the continuous measurement of the volumes, it is possible to compensate for possible drifting.

Pressure Sensor Offset from the Flow Path:

According to FIGS. 11, 12 and 13, the present invention discloses a fluid distribution system (100) (preferably a cassette as described above) by means of which it is possible to sample and/or deliver a fluid F11 from and/or to the patient and to measure the pressure of said fluid F11. The system comprises a rigid body (105) composed of at least one flow path (103), through which said fluid F11 flows, and at least one channel (102). Said channel (102) is separate from the flow path (103) and makes it possible to connect said flow path to a measuring zone (101). The system additionally comprises at least one opening (106) covered by a flexible membrane (104) forming said measuring zone. The membrane is designed to receive a pressure sensor (107).

A fluid F12 different than the fluid F11 is contained in said measuring zone (101). The fluid F12 extends at least in part into said channel (102). Said fluid F12 makes it possible to transmit the pressure of the fluid F11 to said membrane (104) by contact. Said channel (102) is a flow restrictor designed in such a way that said fluid F11 cannot come into contact with said membrane. The length and/or the shape of said pressure transmission channel (102) depends on the expansion capacity of said fluid F12 and/or on the range of pressure to be measured. Preferably, the channel (102) comprises at least one section that is sufficiently narrow to retain the fluid F11 so that said fluid does not enter said measuring zone (101).

In one embodiment, the channel (102) comprises a hydrophobic filter (108) or a membrane.

In one embodiment, an interface of membrane (104)/fluid (F13)/cell of the sensor (107) is created so as to avoid friction by the membrane (104) on said cell, which could create disturbances in the measurement. An interface of liquid (F11)/fluid (F12)/membrane (104) is created in order to avoid the membrane (104) being wetted by the liquid (F11). The transmission of the pressures of F11 is ensured by the fluids F12 and F13 arranged on each side of the membrane (104). F12 and F13 preferably have the same physical properties. Preferably, F12 and F13 are air. Said membrane (104) can deform with equivalent stresses on each side of these faces, so as to compensate for the variations in the volume of air, trapped between the membrane (104) and the sensor (107), due to the temperature.

In another embodiment, the fluid F11 is aqueous, while F12 is lipid, and F13 can be either lipid or aqueous.

In another embodiment, FIG. 13' discloses a fluid distribution system (100) which permits the flow of a fluid F11 and makes it possible to measure the pressure of said fluid F11. The system comprises a rigid body (105) composed of at least one flow path (103), through which said fluid F11 flows, and at least one channel (102). Said channel (102) is separate from the flow path (103) but communicates so that the fluid F11 can flow in the channel (102). Thus, the channel (102) makes it possible to connect said flow path to a measuring zone (101). The system additionally comprises at least one opening (106) covered by a flexible membrane (104) forming said measuring zone. Said opening (106) can be of a size equal to or different than the size of the channel (102). In addition, the membrane is designed to receive a pressure sensor (107). A fluid F12 different than the fluid F11 is contained in said measuring zone (101). The fluid F12 is contained at least in part in the measuring zone and/or in the channel (102).

In an embodiment again illustrated by FIG. 13', the quantity and/or the volume of the fluid F12 is constant or can decrease over the course of time such that the fluid F11 advances with greater or lesser speed in the channel (102) and/or the measuring zone (101).

In one embodiment, the measuring zone (101) and/or the channel (102) contain at least in part the fluid F12 and the fluid F11. The fluid F11 can partially wet or be in contact with the membrane (104). The length and/or the shape of said pressure transmission channel (102) depends on the expansion capacity of said fluid F12 and/or on the range of pressure to be measured.

The channel (102) can be designed in such a way as to limit and/or slow the progress of the fluid F11, for example, during the use of said system. The fluid distribution system (100) can be adapted in such a way as to guarantee that the membrane (104) and/or the measuring zone (101) are not completely wetted by or in contact with the fluid F11 during the use of said system.

Energy-Saving Linear Actuator:

The invention discloses a linear actuator (200) using a motor (for example a direct-current motor (or DC motor) or another type of motor known to a person skilled in the art) (201) coupled to interposed means that make it possible to transform the rotation of the motor shaft into a linear movement. Preferably, the motor can also comprise a torque reducer.

In particular, the interposed means comprise:
at least one peripheral ramp (214) arranged inside a piston (207),
at least one bearing means (209) fixed directly or indirectly to the rotor (208) of said electric motor (201), said bearing means (209) being designed in such a way as to cooperate with said peripheral ramp (214),
at least one guide means (203, 216) allowing the piston (207) to guide the translation movement.

Said ramp (214) comprises at least one threshold, of which one threshold (215) is located at the summit of said ramp (214). In one embodiment, at least one threshold can be designed in such a way as to cooperate with the bearing means. For example, the threshold can be perfectly flat and horizontal with respect to the vertical movement of the piston. The threshold can also have a specific shape for ensuring a good hold of the bearing means in order to guarantee that the position is maintained, for example the embodiment on the right in FIG. 18'. In addition, the threshold (215) located at the summit of said ramp (214) can be followed by a passage (219) allowing the piston (207) to free itself of the stresses exerted by said bearing means (209).

The piston can comprise one or more ramps and/or one or more passages. At least one ramp can have an inclination of between 0 and 90°. In one embodiment, said inclination can be between 0 and 45°, preferably between 10 and 30°.

Said piston (207) comprises at least two stationary positions:
a first position, in which the piston (207) is situated at a distance (d2) equal to A. In this position, the bearing means (209) is located at the start of the ramp;
a second position, in which the piston (207) is situated at a distance (d2) equal to B. In this position, the bearing means (209) cooperates with a threshold allowing the piston to maintain this position.

The system has several advantages:
No need to power the motor in order to keep the valve opened (3rd stable state).
The actuator will not heat when maintaining a position.
Low operating noise.
Substantial travel.

In a preferred embodiment such as is shown in FIG. 16, the piston (207) has at least one ramp (214) (preferably two or more) and the bearing means can be a transverse shaft adapted to cooperate at least temporarily with said at least one ramp. Thus, when the piston comprises two ramps positioned symmetrically with respect to the center of the shaft of the rotor, for one complete turn of the rotor, the piston can on two occasions be at the second position and first position. The piston can comprise a passage (219) permitting a rapid transition from the second position to the first position, and said passage can extend below the first position. This makes it possible:
to obtain two positions of the piston (first and third positions) without actuation of the actuator,
to make assembly easier,
to prevent the rotor (or the motor) from turning when the piston is in the third position, which makes impossible any change of position when the cassette is not loaded in the apparatus.

According to one embodiment, the ramp is followed by at least one passage, preferably after a threshold.

In one embodiment, said actuator additionally comprises at least one compression means (205) exerting a force against the piston (207). The bearing means and the ramp cooperate in order to move the piston on the same axis as the force exerted by the compression means, but in an opposite direction.

In one embodiment, said compression means tends to push the piston back (with respect to the actuator) (that is to say in the direction (220) of the distal end of the piston (217)) while the bearing means and the ramp compel the piston to move toward the actuator. In this case, A>B. In another embodiment, said compression means tends to move the piston toward the actuator while the bearing means and the ramp compel the piston to move away from the actuator. In this case, A<B.

In one embodiment, the aim of the actuator is to drive an element of an apparatus such as that described in the present document. This can be, for example, a valve of the cassette.

The rest of the description describes this embodiment, but it goes without saying that the invention is not limited to this embodiment.

Thus, said piston (207) comprises at least two positions:

a first position, in which the stub (211) of the piston (207) is coupled to the valve (212) (illustration in FIG. 15) of a cassette such as that described above. The piston (207), not constrained by the bearing means (209), maintains the valve (212) in a closed position against the seat of the valve (213). Here, d2 is equal to A.

a second position, in which the stub (211) of the piston (207) is coupled to the valve (212). The piston (207) is constrained by the bearing means (209), moving the piston/stub assembly in the direction (221) of the motor (201). When said bearing means (209) arrives at the threshold (215) situated at the summit of the ramp, the piston (207) is in the second position and the valve (212) is in the opened position. Here, d2 is equal to B.

In one embodiment, the piston has a third position, in which the stub (211) of the piston (207) is decoupled from the valve (212). A compression means (205) exerts a force against the piston, moving said piston toward a third position farther from the motor than the first and second positions. This can be the same compression means as described above or a separate compression means. Here, d2 is equal to C. In this embodiment, C>A>B. The benefit of this third position is to guarantee a sufficient occlusion pressure when the piston is coupled to the valve in the first position. In other words, when the piston is coupled to the valve, the piston exerts a force against the valve in order to ensure the closure of the valve when the piston is in the first position.

In one embodiment, the actuator comprises an element for fixing to its support, comprising a compression means exerting a force in the direction of the distal end of the piston and having the same function as described above.

Said compression means (205) can be a spring, an elastic blade, an elastic material or a shape-memory material. Said compression means (205) can exert a force of 0 to 6 N, preferably of between 5 and 6 N.

The actuator (200) is designed with the aim of not consuming energy while a stationary position is maintained. The bearing means (209) is designed to slide or roll on the ramp in order to reach a position. When the bearing means (209) stops on a threshold, said threshold is designed in such a way that the assembly is at equilibrium. The threshold (215) at the summit of the ramp (214) is directly followed by a passage (219) allowing the piston to pass rapidly from a second position to a first position while consuming a minimum amount of energy. Said passage makes it possible to pass from one position to the other with a small amount of energy. In other words, the energy consumed by the actuator for passing from the first position to the second position is greater than the energy consumed by the actuator for passing from the second position to the first position. The passage (219) can be a ramp having a high slope and/or oppositely directed to the slope of the ramp. Thus, the bearing means travels a shorter distance to pass from the second position to the first position than the other way round.

Optionally, the piston (207) comprises several thresholds in order to have intermediate rest positions.

In one embodiment, the motor comprises a torque reducer between the motor and the rotor of the interposed means. Said torque reducer can be designed in such a way that the motor can turn the rotor but the rotor cannot turn the motor. In other words, the torque reducer, by virtue of its design, can prevent or limit or brake any movement of the rotor that is not due to the motor.

In one embodiment, the torque reducer can be designed in such a way that the actuator can maintain any position when the motor is stationary (powered or not). Thus, the actuator can comprise a limited number of thresholds as described above, but an unlimited number of positions that can be maintained by virtue of the torque reducer without the actuator being fed with current. Such an actuator can be adapted to cooperate with a proportional valve of a fluid distribution cassette. Thus, by means of this design, the actuator can permit the flow of a fluid proportionally to the requirement of the treatment.

In one embodiment, the piston (207) does not comprise any threshold but only positions that can be maintained by virtue of the torque reducer as described above. This piston thus comprises at least one ramp and optionally one passage. The torque reducer allows the actuator to maintain a given position permitting the 0% to 100% opening of a valve (for example a proportional valve).

In one embodiment, the piston comprises at least one lower ramp and upper ramp, said ramps being adapted such that at least one bearing means (209) can move between said ramps. Said ramps can at least in part be parallel with respect to each other.

In a preferred embodiment, at least one actuator is arranged in an actuation system which comprises a controller and at least one power supply means. Said system is designed to move at least one piston from a second position to a first position and vice versa while consuming a small amount of energy. Said power supply means can be an external power supply and/or an energy storage means. Said energy storage means can be used by the system when said external power supply is no longer operative or is inadequate. Thus, in the event of an outage, the valve will move from the open to the closed state by virtue of the use of said energy storage means, which can be a supercapacitor, or a battery.

According to an embodiment disclosed by FIG. 14, the actuator (200) can be composed of:
- a motor (201),
- a rigid envelope (202) inside which are arranged:
  - a sensor (204) fixed to the motor with said envelope (202),
  - a compression means (205),
  - a piston (207) in which is fixed an element (206) designed to cooperate with said sensor (204),
  - a bearing means (209) fixed directly or indirectly to the rotor (208) of the motor (201),
  - an element (210) fixed to the distal end (217) of the piston permits fixation of a stub (211) which will be coupled to a valve.

The piston (207) and the rigid envelope (202) comprise guide means (203, 216) to avoid the piston turning with the rotor (208) of the motor.

FIGS. 17, 18, 19, 20 and 21 show the piston in different positions (the valve and the stub are not shown in these figures):

FIG. 17: The valve is not coupled to the stub. The piston (207) is in the third position with the compression means (205) relaxed. The bearing means (209) is in the passage (219) and does not exert any force against the ramp (214).

FIG. 18: The valve is coupled to the stub. The piston (207) is in the first position, and the compression means (205) exerts a pressure against the piston (207) in order to guarantee the closed position of the valve. Preferably, the bearing means (209) and the ramp (214) do not exert any stress. FIG. 18' reveals two different embodiments of the threshold (215) at the summit of the ramp. Thus, according to one embodiment, said threshold can have a different shape, it can be flat or designed more or less for greater cooperation with the bearing means (209) when the latter is situated near and/or on the threshold (215).

FIG. 19: The valve is coupled to the stub. The rotor (208) is in motion in order to allow the piston (207) to pass from the first position to the second position. The bearing means (209) travels on the ramp (214) and compels the piston (207) to move toward the motor (opening of the valve) and compresses the compression means (205).

FIG. 20: The valve is coupled to the stub. The piston (207) is in the second position, and the bearing means (209) stops on the threshold (215) at the summit of the ramp. The compression means (205) is compressed. The valve is opened. The position is stable without contribution from the motor (201). In one embodiment, the actuator comprises a sensor designed to establish the relative position of the piston (207). The embodiment shown in FIG. 20 reveals a Hall effect sensor (204) cooperating with a magnet (206) housed in the piston. The sensor (204) can be a linear displacement sensor comprising a rod or an encoder or any elements (206) suitable for cooperating with said sensor (204). In addition, by virtue of the processor connected to the sensor (204), it is possible to establish or monitor the position of said piston (207).

FIG. 21: The valve is coupled to the stub. The rotor (208) is in motion, causing the bearing means (209) to move in the passage (219). The piston moves instantaneously from the second position to the first position by virtue of the compression means (205) which pushes the piston (207) back in the direction of the distal end of the piston (217). The valve closes.

Control System, and Control of an Actuator

In an embodiment disclosed by FIGS. 32, 32' and 33, a control system (800) comprises a linear actuator comprising a movable part (801) and a stationary part (804) and also control elements (802, 803, 805). The control elements are adapted to establish the position of the movable part (801) with respect to the stationary part (804) and to control the linear actuator.

FIG. 32 shows the actuator in a position A, and FIG. 32' shows the actuator in a position B. The control element (805) controls the actuator, of which the stationary part (804) can comprise the drive means (for example a motor). The movable part (801) can be adapted to cooperate with, for example, a valve of a fluid distribution system. Thus, the position A could correspond to the closed position of the controlled valve, and the position B could correspond to the opened position of said valve. However, the invention is not limited to controlling the opening and closing of a valve of a fluid distribution system, and the number of positions can be limited or unlimited.

The elements 1 (802) and 2 (803) of the sensor are designed to cooperate and determine at least one position. This can entail a capacitive or inductive displacement sensor (LVDT, etc.), an electromagnetic sensor (Hall effect sensor), ultrasonic sensor, infrared sensor, optical sensor, laser-type sensor, mechanical sensor or microwave sensor (list not exhaustive). In our example, and to aid understanding, we will use a Hall effect sensor. Thus, the element 1 (802) is a permanent magnet (in this case it is not connected to the processor) (805), and the element 2 (803) is a Hall effect sensor connected to the processor. The permanent magnet creates an electromagnetic field, of which the sensor (803) measures the strength. In particular, the sensor (803) makes it possible to detect the variation of the magnetic field induced by the permanent magnet (802) when the latter moves.

Preferably, the permanent magnet (802) is rigidly fixed in a definitive manner to the movable part (801) of the actuator, and the sensor (803) is rigidly fixed in a definitive manner to the stationary part (804) of the actuator (or the other way round). Thus, when the movable part moves, the permanent magnet (802) moves toward or away from the sensor (803), which thus measures a variation in the strength of the magnetic field of the permanent magnet (802). Ideally, the magnet and the sensor are aligned.

The measurement data of the sensor (802) are transmitted to the processor in order to process the signal. Normally, all the control systems have to be graded in order to determine in advance the strength corresponding to each position. In other words, the sensor generally detects predetermined threshold values corresponding to respective positions determined in advance. However, this grading work (for example calibration to be carried out on all the actuators) is lengthy and laborious. To avoid this grading work, the invention discloses the use of a processor that processes the signal in order to determine at least one position of the actuator. Thus, the invention makes it possible to avoid performing a calibration.

The upper graph in FIG. 33 reveals that the absolute value (strength of the electromagnetic field of the magnet measured by the sensor) can be very different from one actuator to another. This is because the sensors of the actuators 1 and 2 do not show the same strength (in absolute value) although their position is identical. Thus, it would be difficult and unreliable, or even impossible, to determine the position of these actuators as a function of a single threshold value.

The control system (800) comprises a processor (805) which uses a mathematical model taking account of the derivative of the absolute value. In the present document, the absolute value is the value measured by the sensor (803) and corresponds to the strength of the magnetic field. The curve of the absolute value is shown by the upper graph in FIG. 33. The derivative of the absolute value is the director coefficient of the curve plotted by the absolute value. In other words, the derivative makes it possible to establish the slope of the variation of the magnetic field when the magnet moves with respect to the sensor. This derivative is shown by the curve in the middle graph of FIG. 33. Thus, this derivative makes it possible to establish the direction of displacement of the movable part (801) of the actuator with respect to its stationary part (804).

The control system thus comprises a processor using a mathematical model that takes account of the derivative of the signal. By virtue of this mathematical model, it is possible to know when the actuator has reached a position or a threshold of the kind described in the section disclosing the linear actuator. Indeed, when the actuator moves its movable part (801), the first derivative is greater or less than 0, but when the actuator does not move its movable part (801), its first derivative is substantially equal to 0. In our example, and by preference, when the magnet (802) moves away from the sensor (803), the first derivative is negative and, inversely, when the magnet moves closer, the first derivative is positive.

The system can additionally comprise a mathematical model for determining when the movable part moves and when it remains immobile. This second mathematical model takes account of the second derivative of the absolute value.

By virtue of this second mathematical model, the system knows when the movable part changes its behavior (movable or immobile).

In one embodiment, the control system comprises an actuator comprising at least one ramp and at least one threshold (for example a linear actuator of the kind described in the present document), and a processor adapted to control the actuator and to process the signal according to at least one mathematical model.

A first mathematical model takes account of the first derivative of the absolute value measured by the sensor (803). The processor can use this first mathematical model in order to establish in which direction the movable part (801) moves. When the first derivative is close to 0, the control system knows that the actuator has reached a threshold.

A second mathematical model takes account of the second derivative of the absolute value measured by the sensor (803). The processor can use the second mathematical model in order to establish when a threshold is reached and/or when the movable part is immobile or moving. The lower graph of FIG. 33 shows the signal resulting from the second mathematical model. When the signal is equal to the value f, this signifies that the actuator maintains a position or is on a threshold. When the signal is equal to the value d, it signifies that the movable part (801) is moving. Thus, by virtue of this second mathematical model, the system has no need of the absolute value. When the control system powers the actuator in order to move its movable part (801), the second mathematical model makes it possible to establish when the actuator has reached a position. In other words, when the actuator continues its actuation (for example it causes the bearing means (209) to turn) but the movable part no longer moves, the processor, by virtue of the first and/or second derivative, is able to establish that the bearing means has reached a threshold. Thus, when the processor orders a change of position of the actuator, a mathematical model allows the processor to know when the threshold is reached and it thus orders the actuator to stop.

Thus, said control system is adapted to determine at least one position reached by the movable part (801) of the actuator independently of the characteristics of the sensor used. Said control system is adapted to stop the actuator at at least one position reached by the movable part (801) of the actuator independently of the characteristics of the sensor used.

In one embodiment, the control system comprises an actuator comprising at least two separate positions. The actuator comprises at least one threshold defining a position, and at least one ramp making it possible to change position. The actuator is driven by a motor designed to turn preferably in a single direction, such that it goes from one position to another sequentially and in a pre-defined order. Preferably, the actuator is adapted to return to its starting position by executing at least one partial revolution. In addition, the processor comprises a mathematical model that takes account of the second derivative of the absolute value measured by said sensor. Said processor comprises a memory which contains the sequence of the positions, such that said system does not need to know the first derivative of the absolute value in order to know the position of the actuator. It suffices for the actuator to execute one revolution in order to know with precision its position, for example during the start-up of the system.

Drive Device used for the Peristaltic Pumps:
In one embodiment, the treatment system can comprise a drive device used for the peristaltic pumps. Said drive device disclosed by the present document can also be used by diverse peristaltic pumps and/or fluid distribution systems comprising a peristaltic pump.

The invention also discloses a method for correcting the tolerance errors of the shaft driving the peristaltic pumps. Said invention, presented in FIGS. 22 and 23, is a drive device (300) which comprises a floating shaft (301) driven by a drive means (303) fixed to a rotor (310) of an electric motor (not shown). Said floating shaft (301) comprises a rigid assembly of base (311) and cover (302) forming a cavity inside which said drive means (303) is at least partially circumscribed. Said drive means (303) comprises a rigid body designed in such a way as to cooperate with the walls (309, 309') of said cavity (313), so as to permit a limited freedom of the floating shaft (301) with respect to the axis of said rotor (310). A screw (307) can permit fixing of the drive means (303) to said rotor (310).

The cavity comprises at least one cooperation element (312), which allows said drive means (303) to transmit a rotation movement to said floating shaft.

Preferably, said cooperation element (312) is an opening limited by two hard elements (308) and through which a shaft (306) is housed perpendicularly. The space between the two hard elements (308) is reasonably greater than the diameter of the shaft (306).

The hard elements (308) and/or the shaft (306) can be made from hard metals such as cobalt, tungsten, vanadium, chromium, manganese, nickel, titanium, germanium, gallium, bismuth, indium, lithium, magnesium, molybdenum, strontium, rubidium or palladium. In one embodiment, the hard elements (308) have a greater hardness than the shaft (306). The hard elements (308) and/or the shaft (306) can be treated to increase their hardness, for example with zirconium oxide or one of its alloys.

In one embodiment, the body (304) of said drive means (303) can be of a spherical shape that is perfectly round or partially flattened. In another embodiment, said body (304) forms a roller comprising three faces. Two of the three faces lie opposite each other and are interconnected by way of the third face, which is curved. On the plane X-Z, said roller forms a circle formed by said curved face. The connection between at least one of the two faces lying opposite each other and the curved face can be rounded on the plane X-Y. The faces lying opposite each other can be substantially plane and/or substantially parallel with respect to each other.

In one embodiment, the cavity (313) comprises three smooth walls (309, 309'). Preferably, the upper wall (309) and/or the lower wall (309') of said cavity (313) are of at least partially conical shape. The surfaces of the upper wall (309) and of the lower wall (309') can be plane or curved.

In one embodiment, on the plane X-Y, the cone of the smooth wall (309) is defined according to an angle of between 0 and 90°, preferably of between 5 and 30°. The cone of the opposite smooth wall (309') is defined according to an angle of between −0 and −90°, preferably of between −5 and −30°. The angles of the two partial cones can be equal or different.

The smooth walls (309, 309') are adapted to cooperate with the ends of the body (304) such that the floating shaft (301) can move on at least three axes X, Y or Z and/or can undergo pitching movements. For example, on the axis Y, the floating shaft (301) can undergo a pitching movement of +/−10°, preferably of +/−5°.

In one embodiment, the drive means (303) comprises a longitudinal shaft (305) and the floating shaft (301) comprises a second cavity (313'), which extends along the floating shaft. The longitudinal shaft (305) fits inside the second cavity (313') in order to restrict the pitching movements of the floating shaft (301). Generally speaking, and preferably, the dimensions of the elements forming the drive means (303, 306, 305) are reasonably smaller than the elements forming the inside of the floating shaft (301, 302, 313, 312).

In one embodiment, the drive system (300) comprises a drive shaft which is formed in one piece, extends on the axis Y and is adapted to drive at least one roller (320) of a peristaltic pump system. said roller is adapted to crush a flexible tube (not shown) against a wall (not shown). According to FIGS. 22 and 23, the drive shaft is represented by the floating shaft (301). In other words, the drive shaft can be the floating shaft and/or merged with a part of the drive system. According to FIGS. 22 and 23, the drive shaft can be of cylindrical shape and comprise a beveled free end (here the term free end is the opposite of the opposite end connected directly or indirectly to the motor). The cylinder of the drive shaft forms a circle on a plane X-Z.

In one embodiment, said drive shaft is formed in one piece composed of at least two different cylinders that are defined by the same axis (in other words center of the cylinder) but have different diameters. Thus, on the plane X-Z, the drive shaft can form at least two circles that are parallel but of different sizes. In addition, the drive shaft can comprise three cylinders of which one alone is of a different diameter. The cylinder defined by the smallest diameter can be arranged between the two cylinders of equal diameter. Said cylinders of greater diameter can have surfaces that are treated in such a way as to improve the cooperation with the rollers of the peristaltic pump.

This construction of the drive shaft with three cylinders is particularly suitable and of advantage for the use of an H-shaped roller, such as the roller (320) of FIG. 23. The roller is arranged in a peristaltic pump system and will crush a flexible tube. The function of crushing is preferably effected by a rigid part (322) of the roller (320). Said roller (320) is a cylinder forming a circle on the plane X-Z and comprises a shaft (321) at the center of this cylinder that extends on the axis Y, a rigid part (322), and at least one flexible part (323) which is deformable. The flexible part is adapted to cooperate with the drive shaft.

Preferably, the cylinders of greater diameter come into contact with the flexible parts (323) of the roller (320) and drive the roller (320). When the drive shaft is in contact with at least one flexible part, said flexible part (323) can deform in order to improve the cooperation between these two elements and/or to adjust the tolerance errors of each of these elements.

Preferably, the roller comprises a rigid part (322) at its center and two flexible parts (323) at the ends on the axis Y.

A fluid distribution system comprising a floating shaft (301), a drive shaft with three cylinders and/or a roller with rigid and flexible parts makes it possible to substantially improve the cooperation between roller and drive shaft and to correct the tolerance errors of the various elements of the system.

Means for Damping the Pressure Peaks:

In one embodiment, the treatment system comprises at least one means for damping the pressure peaks.

FIG. 24 shows the pressure signal measured near the inlet of a peristaltic pump. On the first curve (401), it is possible to observe the oscillation of the pressure, while the second curve (402) represents the mean value of this pressure. The aim of the damper is to reduce the amplitude of the oscillations of the first curve (401).

Such a damping means can be installed in one or more flow paths of a distribution system as described above. Preferably, this damping means is integrated in a cassette.

Whether in peritoneal dialysis or continuous renal replacement therapy, each treatment has one or more possible configurations. The phenomenon of pressure peaks can be amplified or attenuated by various elements that vary according to said configurations. It will be recalled that one of the objects of the invention is to permit simple use of the system. Therefore, reproducibility is an important element, since the operator (generally the nurse) must be able to ensure correct operation of the system without having to take into account the characteristics of the different elements.

The distribution system as disclosed in this document is a cassette through which fluids flow in three flow paths. Preferably, they are propelled by peristaltic pumps. Reproducibility, precision and patient comfort are important elements. Thus, at least one damping means is preferably integrated in said cassette. To be as effective as possible, said damping means must be placed as close as possible to the pumping system.

In an embodiment depicted schematically in FIG. 25, the flow path comprises walls (404) delimiting said path. These walls can be the rigid walls of the cassette. A section of the flow path is covered by a flexible membrane (403), which then replaces said wall (404). By virtue of the elasticity of said flexible membrane (403), the pressure peaks are substantially attenuated, absorbed by the deformation of the membrane (403). The absorption of these peaks depends on the size and elastic characteristics of the membrane.

In another embodiment, depicted schematically in FIG. 26, the flow path likewise comprises walls delimiting said path, but a section is replaced by a cavity filled with a compressible fluid such as air. This air may have been trapped (about 1 ml) during the priming of the system. Thus, the volume of the air is compressed to a greater or lesser extent during the pumping, absorbing the energy of the pressure peaks. This embodiment is particularly effective since it requires little energy for its operation, and said fluid very rapidly absorbs the pressure peaks. Preferably, the cavity or the inlet of the cavity is designed to avoid the compressible fluid completely escaping. In other words, the cavity is designed to ensure that the flowing fluid does not replace the compressible fluid.

Preferably, said damping means is placed upstream of the pumping mechanism.

The invention claimed is:

1. A medical pump system comprising:
   a disposable cassette having a pump; and
   a reusable apparatus having a drive device configured to cooperate with the pump of the disposable cassette,
   wherein the drive device includes a floating shaft having a rotational axis rotatably driven by a drive means, the drive means configured to be coupled to a motor rotor having a motor axis of the reusable apparatus,
   wherein the floating shaft includes a cavity inside which the drive means is at least partially circumscribed,
   wherein the drive means includes a body configured to cooperate with internal walls of the cavity to limit an orientational freedom of the rotational axis of the floating shaft relative to the motor axis to compensate for tolerance errors of the pump, and
   wherein the cavity includes a cooperation element allowing the drive means to apply a rotation movement to the floating shaft.

2. The medical pump system as claimed in claim 1, wherein the body of the drive means includes smooth rounded edges and the cavity includes smooth walls.

3. The medical pump system as claimed in claim 1, wherein the drive means includes a longitudinal shaft, and the floating shaft includes an additional cavity extending along the floating shaft, the longitudinal shaft located inside the additional cavity to limit lateral movements of the floating shaft.

4. The medical pump system as claimed in claim 1, wherein the drive means includes a transversal shaft, and the cooperation element includes two hard elements,
wherein the transversal shaft is configured to engage with the two hard elements of the cooperation element for applying the rotational movement.

5. The medical pump system as claimed in claim 4, wherein at least one of the hard elements of the cooperation element and the transversal shaft of the drive means is made of a composition including an element selected from the group including cobalt, tungsten, vanadium, chromium, manganese, nickel, titanium, germanium, gallium, bismuth, indium, lithium, magnesium, molybdenum, strontium, rubidium, and palladium.

6. The medical pump system as claimed in claim 1, wherein the internal walls of the cavity are configured to cooperate with external walls of the body of the drive means to allow the floating shaft to move linearly relative to the drive means.

7. The medical pump system as claimed in claim 1, wherein the internal walls of the cavity are configured to cooperate with external walls of the body to allow the rotational axis of the floating shaft to undergo pitching movements relative to motor axis between +/−10°.

8. The medical pump system as claimed in claim 1, wherein the internal walls of the cavity are configured to cooperate with external walls of the body of the drive means to allow the rotational axis of the floating shaft to undergo pitching movements relative to the motor axis between +/−5°.

9. The medical pump system as claimed in claim 1, wherein the internal walls of the cavity includes a cone shape having a cone angle of between 0° and 90°.

10. The medical pump system as claimed in claim 1, wherein the internal walls of the cavity includes a cone shape having a cone angle of between 5° and 30°.

11. The medical pump system as claimed in claim 1, wherein the pump includes a peristatic pump including a flexible tube and a roller, the floating shaft configured to operationally engage with the roller of the peristaltic pump.

12. The medical pump system as claimed in claim 11, wherein the roller includes a flexible part configured to cooperate with the floating shaft.

13. The medical pump system as claimed in claim 1, wherein the floating shaft includes a rigid assembly having base and a cover, the cover forming the cavity.

14. The medical pump system as claimed in claim 1, wherein the drive means includes a transversal shaft, and the internal walls of the cavity include two walls arranged above and below the transversal shaft, the two walls having a conical shape.

15. A medical pump system comprising:
a disposable cassette having a pump; and
a reusable apparatus having a drive device configured to cooperate with the pump of the disposable cassette,
wherein the drive device includes a floating shaft having a rotational axis rotatably driven by a drive means, the drive means configured to be coupled to a motor rotor having a motor axis of the reusable apparatus,
wherein the floating shaft includes a cavity inside which the drive means is at least partially circumscribed,
wherein the drive means includes a body configured to cooperate with internal walls of the cavity to limit an orientational freedom of the rotational axis of the floating shaft relative to the motor axis to compensate for tolerance errors of the pump, and
wherein the internal walls of the cavity are configured to cooperate with external walls of the body to allow the rotational axis of the floating shaft to undergo pitching movements relative to motor axis between +/−10°.

16. A medical pump system comprising:
a disposable cassette having a pump; and
a reusable apparatus having a drive device configured to cooperate with the pump of the disposable cassette,
wherein the drive device includes a floating shaft having a rotational axis rotatably driven by a drive means, the drive means configured to be coupled to a motor rotor having a motor axis of the reusable apparatus,
wherein the floating shaft includes a cavity inside which the drive means is at least partially circumscribed,
wherein the drive means includes a body configured to cooperate with internal walls of the cavity to limit an orientational freedom of the rotational axis of the floating shaft relative to the motor axis to compensate for tolerance errors of the pump, and
wherein the internal walls of the cavity includes a cone shape having a cone angle of between 0° and 90°.

* * * * *